US010745455B2

(12) United States Patent
Jain

(10) Patent No.: US 10,745,455 B2
(45) Date of Patent: Aug. 18, 2020

(54) ENDOTHELIN-1 RECEPTOR BASED ENDOTHELIN-1 SPONGE

(71) Applicant: Arjun Jain, Gurgaon (IN)

(72) Inventor: Arjun Jain, Gurgaon (IN)

(*) Notice: Subject to any disclaimer, the term of this patent is extended or adjusted under 35 U.S.C. 154(b) by 127 days.

(21) Appl. No.: 16/039,655

(22) Filed: Jul. 19, 2018

(65) Prior Publication Data

US 2019/0016773 A1    Jan. 17, 2019

Related U.S. Application Data

(63) Continuation-in-part of application No. PCT/IB2016/050337, filed on Jan. 22, 2016.

(51) Int. Cl.

| C07K 16/46 | (2006.01) |
|---|---|
| C12N 15/00 | (2006.01) |
| C07K 14/00 | (2006.01) |
| A61K 38/00 | (2006.01) |
| C07K 14/575 | (2006.01) |
| C07K 14/72 | (2006.01) |
| A61P 9/10 | (2006.01) |
| A61P 25/28 | (2006.01) |
| A61P 3/10 | (2006.01) |
| A61K 47/00 | (2006.01) |
| C07K 14/735 | (2006.01) |
| C12N 15/113 | (2010.01) |
| C12N 15/62 | (2006.01) |
| A61K 38/16 | (2006.01) |

(52) U.S. Cl.
CPC ........ *C07K 14/57536* (2013.01); *A61K 47/00* (2013.01); *A61P 3/10* (2018.01); *A61P 9/10* (2018.01); *A61P 25/28* (2018.01); *C07K 14/70535* (2013.01); *C07K 14/72* (2013.01); *C12N 15/113* (2013.01); *C12N 15/62* (2013.01); *A61K 38/16* (2013.01); *C07K 2317/52* (2013.01); *C07K 2318/10* (2013.01); *C07K 2319/30* (2013.01)

(58) Field of Classification Search
None
See application file for complete search history.

(56) References Cited

U.S. PATENT DOCUMENTS

| 5,589,466 A | 12/1996 | Felgner et al. |
|---|---|---|
| 5,973,972 A | 10/1999 | Kwon et al. |
| 6,077,835 A | 6/2000 | Hanson et al. |

FOREIGN PATENT DOCUMENTS

| WO | 00/18932 A2 | 4/2000 |
|---|---|---|
| WO | 00/70087 A1 | 11/2000 |
| WO | 00/75319 A1 | 12/2000 |
| WO | 03/092610 A2 | 11/2003 |
| WO | 2004/039951 A2 | 5/2004 |
| WO | 2006/113614 A2 | 10/2006 |

OTHER PUBLICATIONS

Justice et al. Using the mouse to model human disease: increasing validity and reproducibility. Disease, Models & Mechanisms 9:101-103 (2016). (Year: 2016).*
Alexander et al. (Endothelin Type A Receptor Blockade Attenuates the Hypertension in Response to Chronic Reductions in Uterine Perfusion Pressure. Hypertension vol. 37[part 2]:485-489, (2001). (Year: 2001).*
Czajkowsky et al., Fc-fusion proteins: new developments and future perspectives, EMBO Mol Med., 4:1015-1028 (2012).
Jain et al., Endothelin-1-Induced Endoplasmic Reticulum Stress in Disease, Journal of Pharmacology and Experimental Therapeutics, 346, 163-172 (2013).
Huang et al., Receptor-Fc fusion therapeutics, traps, and MIMETIBODY (TM) technology, Current Opinion in Biotechnology, 20, 692-699 (2009).
Wada et al., Ligand Binding Domain of the Human Endothelin-B Subtype Receptor, Protein Expr Purif 6, 228-236 (1995).
Klammt et al. Functional analysis of cell-free-produced human endothelin B receptor reveals transmembrane segment 1 as an essential area for ET-1 binding and homodimer formation, FEBS J 274, 3257-3269 (2007).
Orry and Wallace, Modeling and Docking the Endothelin G-Protein-Coupled Receptor, Biophys J 79, 3083-3094 (2000).
Adachi et al, Funcitional domains of human endothelin receptor, J Cardiovasc Pharmacol 22 Suppl 8: S121-124 (1993).
Economides et al, Cytokine traps: multi-component, high-affinity blockers of cytokine action, Nature Medicine, 9, 47-52 (2002).
Schwache et al., Receptor fusion proteins for the inhibition of cytokines, European Journal of Cell Biology, 91, 428-434 (2012).
Nelson et al., The Endothelin Axis:Emerging Role in Cancer, Nat Rev Cancer 3, 110-116 (2003).
Jain et al, Endothelin-1 Induces Endoplasmic Reticulum Stress by Activating the PLC-IP3 Pathway, Am J Pathol 180, 2309-2320 (2012).
Karet and Davenport, Endothelin and the human kidney: a potential target for new drugs, Nephrol Dial Transplant 9, 465-468 (1994).
Jain et al, Endothelin-1-induced endoplasmic reticulum stress in Parkinson's Disease, Pharmacologia, 5, 84-90 (2014).
Zeiher et al., Tissue Endothelin-1 Immunoreactivity in the Active Coronary Atherosclerotic Plaque, Circulation 91, 941-947 (1995).
Seligman et al., Increased Plasma Levels of Endothelin 1 and von Willebrand Factor in Patients With Type 2 Diabetes and Dyslipidemia, Diabetes Care 23, 1395-1400 (2000).
Schneider et al., Elevated Plasma Endothelin-1 Levels in Diabetes Mellitus, Am J Hypertens 15, 967-972 (2002).
Haufschild et al., Increased Endothelin-1 Plasma Levels in Patients With Multiple Sclerosis, J Neuroophthalmol 21, 37-38 (2001).

(Continued)

*Primary Examiner* — Joanne Hama
*Assistant Examiner* — Regina M DeBerry
(74) *Attorney, Agent, or Firm* — Browdy and Neimark, PLLC

(57) ABSTRACT

Fusion polypeptides capable of binding endothelin-1 to form a non-functional complex are provided, including amino acid sequences of the fusion polypeptides. The fusion polypeptides will be linked to the Fe portion of human IgG I to form dimers that will function as endothelin-1 antagonists (endothelin-1 sponge).

9 Claims, 34 Drawing Sheets

Specification includes a Sequence Listing.

(56) References Cited

OTHER PUBLICATIONS

Pache et al., Extraocular Blood Flow and Endothelin-1 Plasma Levels in Patients with Multiple Sclerosis, Eur Neurol 49, 164-168 (2003).
Sethi et al., Homocysteine-induced endothelin-1 release is dependent on hyperglycaemia and reactive oxygen species production in bovine aortic endothelial cells, J Vasc Res 43, 175-183 (2006).
Wang et al., Discovery of Dual ETA/ETB Receptor Antagonists from Traditional Chinese Herbs through in Silico and in Vitro Screening, Int J Mol Sci, 17, 389 (2016).
Jain, Endothelin-1: a key pathological factor in pre-eclampsia?, Reprod Biomed Online, 25, 443-449 (2012).
George and Granger, Endothelin: Key Mediator of Hypertension in Preeclampsia, Am J Hpyertens, 24, 964-969 (2011).
Saleh et al, The emerging role of endothelin-1 in the pathogenesis of pre-eclampsia, Therpeutic Advances in Cardiovascular Disease, 10, 282-293 (2015).
Böhm et al., The importance of endothelin-1 for vascular dysfunction in cardiovascular disease, Cardiovascular Research, 76, 8-18 (2007).
Jain et al., Creating a Soluble Binder to Endothelin-1 Based on the Natural Ligand Binding Domains of the Endothelin-1 (G-Protein-Coupled) Receptor, International Journal of Peptide Research and Therapeutics (2017).
Huston et al., Protein engineering of antibody binding sites: Recovery of specific activity in an anti-digoxin single-chain Fv analogue produced in *Escherichia coli*, PNAS, 85:16:5879-83 (1988).
Robinson & Bates, Optimizing the stability of single-chain proteins by linker length and composition mutagenesis, PNAS 95, 5929-34 (1998).
Arai et al ., Design of the linkers which effectively separate domains of a bifunctional fusion protein, PEDS, 14, 529-32 (2001).
Chen et al, Fusion Protein Linkers: Property, Design and Functionality, Advanced Drug Delivery Reviews 65, 1357-1369 (2013).
Van Heeke & Schuster, The N-terminal Cysteine of Human Asparagine Synthetase Is Essential for Glutaminedependent Activity, J Biol Chem, 264, 19475-19477 (1989).
Kost and Condreay, Recombinant baculoviruses as expression vectors for insect and mammalian cells, Current Opinion in Biotechnology 10, 428-33 (1999).
Daugherty and Msrny, Formulation and delivery issues for monoclonal antibody therapeutics, Adv Drug Delivery Rev, 58, 686-706 (2006).
Jain et al., Endothelin-1: A potential pathological factor in Parkinson's disease?—From endoplasmic reticulum stress to beyond, Journal of Neurological Sciences, 344, 236-237 (2014).
Gregan et al., Ligand-dependent Differences in the Internalization of Endothelin A and Endothelin B Receptor Heterodimers* The Journal of Biological Chemistry, pp. 27679-27687, vol. 279, No. 26, Issue of Jun. 25 (Apr. 2004).

* cited by examiner

ETA receptor ligand–binding domains

N terminus (Asp21 → Lys80)
Asp-Asn-Pro-Glu-Arg-Tyr-Ser-Thr-Asn-Leu-Ser-Asn-His-Val-Asp-Asp-Phe-Thr-Thr-Phe-Arg-Gly-Thr-Glu-Leu-Ser-Phe-Leu-Val-Thr-Thr-His-Gln-Pro-Thr-Asn-Leu-Val-Leu-Pro-Ser-Asn-Gly-Ser-Met-His-Asn-Tyr-Cys-Pro-Gln-Gln-Thr-Lys-Ile-Thr-Ser-Ala-Phe-Lys

Extracellular loop 1 (Lys140 → Cys158)
Lys-Leu-Leu-Ala-Gly-Arg-Trp-Pro-Phe-Asp-His-Asn-Asp-Phe-Gly-Val-Phe-Leu-Cys

Extracellular loop 2 (Pro228 → Asp256)
Pro-Phe-Glu-Tyr-Arg-Gly-Glu-Gln-His-Lys-Thr-Cys-Met-Leu-Asn-Ala-Thr-Ser-Lys-Phe-Met-Glu-Phe-Tyr-Gln-Asp-Val-Lys-Asp

Extracellular loop 3 (Val332 → Leu347)
Val-Tyr-Asn-Glu-Met-Asp-Lys-Asn-Arg-Cys-Glu-Leu-Leu-Ser-Phe-Leu

Intracellular loop 3 (Thr279 → Cys310)
Thr-Cys-Glu-Met-Leu-Asn-Arg-Arg-Asn-Gly-Ser-Leu-Arg-Ile-Ala-Leu-Ser-Glu-His-Leu-Lys-Gln-Arg-Arg-Glu-Val-Ala-Lys-Thr-Val-Phe-Cys

C terminus (Ser373 → Asn427):
Ser- Lys- Lys-Phe-Lys-Asn-Cys-Phe-Gln-Ser-Cys-Leu-Cys-Cys-Cys-Cys-Tyr-Gln-Ser-Lys-Ser-Leu-Met-Thr-Ser-Val-Pro-Met-Asn-Gly-Thr-Ser-Ile-Gln-Trp-Lys-Asn-His-Asp-Gln-Asn-Asn-His-Asn-Thr-Asp-Arg-Ser-Ser-His-Lys-Asp-Ser-Met-Asn

Figure 1

ETB receptor ligand-binding domains

N terminus + Intracellular loop 1 (Pro93 → Cys131):
Pro-Ile-Glu-Ile-Lys-Glu-Thr-Phe-Lys-Tyr-Ile-Asn-Thr-Val-Val-Ser-Cys-Leu-Val-Phe-Val-Leu-Gly-Ile-Ile-Gly-Asn-Ser-Thr-Leu-Leu-Arg-Ile-Ile-Tyr-Lys-Asn-Lys-Cys

C terminus (Ser390 → Leu401):
Ser-Lys-Arg-Phe-Lys-Asn-Cys-Phe-Lys-Ser-Cys-Leu

Transmembrane domains 2 + 3 (Ile138 → Ile197):
Ile-Leu-Ile-Ala-Ser-Leu-Ala-Leu-Gly-Asp-Leu-Leu-His-Ile-Val-Ile-Asp-Ile-Pro-Ile-Asn-Val-Tyr-Lys-Leu-Leu-Ala-Glu-Asp-Trp-Pro-Phe-Gly-Ala-Glu-Met-Cys-Lys-Leu-Val-Pro-Phe-Ile-Gln-Lys-Ala-Ser-Val-Gly-Ile-Thr-Val-Leu-Ser-Leu-Cys-Ala-Leu-Ser-Ile

Figure 2

SEQ ID NO: 1

Val Tyr Asn Glu Met Asp Lys Asn Arg Cys Glu Leu Leu Ser
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
                        ETAR

Phe Leu | Ser Lys Lys Phe Lys Asn Cys Phe Gln Ser Cys Leu
⎯⎯⎯⎯⎯▶⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
  ETAR           ETAR

Cys Cys Cys Cys Tyr Gln Ser Lys Ser Leu Met Thr Ser Val
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
                        ETAR

Pro Met Asn Gly Thr Ser Ile Gln Trp Lys Asn His Asp Gln
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
                        ETAR

Asn Asn His Asn Thr Asp Arg Ser Ser His Lys Asp Ser Met
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
                        ETAR

Asn | Lys Thr His Thr Cys Pro Pro Cys Pro Ala Pro Glu Leu
⎯⎯▶⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
ETAR            Fc IgG1

Leu Gly Gly Pro Ser Val Phe Leu Phe Pro Pro Lys Pro Lys
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
                        Fc IgG1

Asp Thr Leu Met Ile Ser Arg Thr Pro Glu Val Thr Cys Val
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
                        Fc IgG1

Val Val Asp Val Ser His Glu Asp Pro Glu Val Lys Phe Asn
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
                        Fc IgG1

Trp Tyr Val Asp Gly Val Glu Val His Asn Ala Lys Thr Lys
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
                        Fc IgG1

Pro Arg Glu Glu Gln Tyr Asn Ser Thr Tyr Arg Val Val Ser
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
                        Fc IgG1

Val Leu Thr Val Leu His Gln Asp Trp Leu Asn Gly Lys Glu
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
                        Fc IgG1

Tyr Lys Cys Lys Val Ser Asn Lys Ala Leu Pro Ala Pro Ile
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
                        Fc IgG1

Figure 6B

SEQ ID NO: 1

Glu Lys Thr Ile Ser Lys Ala Lys Gly Gln Pro Arg Glu Pro
─────────────────────────────────────────────────▶
                    Fc IgG1

Gln Val Tyr Thr Leu Pro Pro Ser Arg Glu Glu Met Thr Lys
─────────────────────────────────────────────────▶
                    Fc IgG1

Asn Gln Val Ser Leu Thr Cys Leu Val Lys Gly Phe Tyr Pro
─────────────────────────────────────────────────▶
                    Fc IgG1

Ser Asp Ile Ala Val Glu Trp Glu Ser Asn Gly Gln Pro Glu
─────────────────────────────────────────────────▶
                    Fc IgG1

Asn Asn Tyr Lys Thr Thr Pro Pro Val Leu Asp Ser Asp Gly
─────────────────────────────────────────────────▶
                    Fc IgG1

Ser Phe Phe Leu Tyr Ser Lys Leu Thr Val Asp Lys Ser Arg
─────────────────────────────────────────────────▶
                    Fc IgG1

Trp Gln Gln Gly Asn Val Phe Ser Cys Ser Val Met His Glu
─────────────────────────────────────────────────▶
                    Fc IgG1

Ala Leu His Asn His Tyr Thr Gln Lys Ser Leu Ser Leu Ser
─────────────────────────────────────────────────▶
                    Fc IgG1

Pro Gly Lys
──────────▶
  Fc IgG1

┆ : Linker / connecting sequence (if any)

Figure 6C

SEQ ID NO: 2

Pro Val Leu Asp Ser Asp Gly Ser Phe Phe Leu Tyr Ser Lys
———————————————————————————————————————————→
Fc IgG1

Leu Thr Val Asp Lys Ser Arg Trp Gln Gln Gly Asn Val Phe
———————————————————————————————————————————→
Fc IgG1

Ser Cys Ser Val Met His Glu Ala Leu His Asn His Tyr Thr
———————————————————————————————————————————→
Fc IgG1

Gln Lys Ser Leu Ser Leu Ser Pro Gly Lys
———————————————————————————————→
Fc IgG1

┊ : Linker / connecting sequence (if any)

Figure 7C

SEQ ID NO: 3

Ser Lys Lys Phe Lys Asn Cys Phe Gln Ser Cys Leu Cys Cys
— ETAR →

Cys Cys Tyr Gln Ser Lys Ser Leu Met Thr Ser Val Pro Met
— ETAR →

Asn Gly Thr Ser Ile Gln Trp Lys Asn His Asp Gln Asn Asn
— ETAR →

His Asn Thr Asp Arg Ser Ser His Lys Asp Ser Met Asn | Lys
— ETAR → | Fc IgG1 →

Thr His Thr Cys Pro Pro Cys Pro Ala Pro Glu Leu Leu Gly
— Fc IgG1 →

Gly Pro Ser Val Phe Leu Phe Pro Pro Lys Pro Lys Asp Thr
— Fc IgG1 →

Leu Met Ile Ser Arg Thr Pro Glu Val Thr Cys Val Val Val
— Fc IgG1 →

Asp Val Ser His Glu Asp Pro Glu Val Lys Phe Asn Trp Tyr
— Fc IgG1 →

Val Asp Gly Val Glu Val His Asn Ala Lys Thr Lys Pro Arg
— Fc IgG1 →

Glu Glu Gln Tyr Asn Ser Thr Tyr Arg Val Val Ser Val Leu
— Fc IgG1 →

Thr Val Leu His Gln Asp Trp Leu Asn Gly Lys Glu Tyr Lys
— Fc IgG1 →

Cys Lys Val Ser Asn Lys Ala Leu Pro Ala Pro Ile Glu Lys
— Fc IgG1 →

Thr Ile Ser Lys Ala Lys Gly Gln Pro Arg Glu Pro Gln Val
— Fc IgG1 →

Figure 8B

SEQ ID NO: 3

Tyr Thr Leu Pro Pro Ser Arg Glu Glu Met Thr Lys Asn Gln
———————————————————————————————————————————————▶
Fc IgG1

Val Ser Leu Thr Cys Leu Val Lys Gly Phe Tyr Pro Ser Asp
———————————————————————————————————————————————▶
Fc IgG1

Ile Ala Val Glu Trp Glu Ser Asn Gly Gln Pro Glu Asn Asn
———————————————————————————————————————————————▶
Fc IgG1

Tyr Lys Thr Thr Pro Pro Val Leu Asp Ser Asp Gly Ser Phe
———————————————————————————————————————————————▶
Fc IgG1

Phe Leu Tyr Ser Lys Leu Thr Val Asp Lys Ser Arg Trp Gln
———————————————————————————————————————————————▶
Fc IgG1

Gln Gly Asn Val Phe Ser Cys Ser Val Met His Glu Ala Leu
———————————————————————————————————————————————▶
Fc IgG1

His Asn His Tyr Thr Gln Lys Ser Leu Ser Leu Ser Pro Gly
———————————————————————————————————————————————▶
Fc IgG1

Lys
——▶
Fc IgG1

┆ : Linker / connecting sequence (if any)

Figure 8C

SEQ ID NO: 4

Pro Ala Pro Glu Leu Leu Gly Gly Pro Ser Val Phe Leu Phe
Fc IgG1

Pro Pro Lys Pro Lys Asp Thr Leu Met Ile Ser Arg Thr Pro
Fc IgG1

Glu Val Thr Cys Val Val Val Asp Val Ser His Glu Asp Pro
Fc IgG1

Glu Val Lys Phe Asn Trp Tyr Val Asp Gly Val Glu Val His
Fc IgG1

Asn Ala Lys Thr Lys Pro Arg Glu Glu Gln Tyr Asn Ser Thr
Fc IgG1

Tyr Arg Val Val Ser Val Leu Thr Val Leu His Gln Asp Trp
Fc IgG1

Leu Asn Gly Lys Glu Tyr Lys Cys Lys Val Ser Asn Lys Ala
Fc IgG1

Leu Pro Ala Pro Ile Glu Lys Thr Ile Ser Lys Ala Lys Gly
Fc IgG1

Gln Pro Arg Glu Pro Gln Val Tyr Thr Leu Pro Pro Ser Arg
Fc IgG1

Glu Glu Met Thr Lys Asn Gln Val Ser Leu Thr Cys Leu Val
Fc IgG1

Lys Gly Phe Tyr Pro Ser Asp Ile Ala Val Glu Trp Glu Ser
Fc IgG1

Asn Gly Gln Pro Glu Asn Asn Tyr Lys Thr Thr Pro Pro Val
Fc IgG1

Leu Asp Ser Asp Gly Ser Phe Phe Leu Tyr Ser Lys Leu Thr
Fc IgG1

Figure 9B

SEQ ID NO: 4

Val Asp Lys Ser Arg Trp Gln Gln Gly Asn Val Phe Ser Cys
———————————————————————————————————▶
                         Fc IgG1

Ser Val Met His Glu Ala Leu His Asn His Tyr Thr Gln Lys
———————————————————————————————————▶
                         Fc IgG1

Ser Leu Ser Leu Ser Pro Gly Lys
———————————————▶
          Fc IgG1

┆ : Linker / connecting sequence (if any)

Figure 9C

SEQ ID NO: 5

Cys Cys Cys Tyr Gln Ser Lys Ser Leu Met Thr Ser Val Pro
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
ETAR

Met Asn Gly Thr Ser Ile Gln Trp Lys Asn His Asp Gln Asn
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
ETAR

Asn His Asn Thr Asp Arg Ser Ser His Lys Asp Ser Met Asn
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
ETAR

Lys Thr His Thr Cys Pro Pro Cys Pro Ala Pro Glu Leu Leu
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
Fc IgG1

Gly Gly Pro Ser Val Phe Leu Phe Pro Pro Lys Pro Lys Asp
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
Fc IgG1

Thr Leu Met Ile Ser Arg Thr Pro Glu Val Thr Cys Val Val
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
Fc IgG1

Val Asp Val Ser His Glu Asp Pro Glu Val Lys Phe Asn Trp
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
Fc IgG1

Tyr Val Asp Gly Val Glu Val His Asn Ala Lys Thr Lys Pro
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
Fc IgG1

Arg Glu Glu Gln Tyr Asn Ser Thr Tyr Arg Val Val Ser Val
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
Fc IgG1

Leu Thr Val Leu His Gln Asp Trp Leu Asn Gly Lys Glu Tyr
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
Fc IgG1

Lys Cys Lys Val Ser Asn Lys Ala Leu Pro Ala Pro Ile Glu
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
Fc IgG1

Lys Thr Ile Ser Lys Ala Lys Gly Gln Pro Arg Glu Pro Gln
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
Fc IgG1

Val Tyr Thr Leu Pro Pro Ser Arg Glu Glu Met Thr Lys Asn
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
Fc IgG1

Figure 10B

SEQ ID NO: 5

Gln Val Ser Leu Thr Cys Leu Val Lys Gly Phe Tyr Pro Ser
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
Fc IgG1

Asp Ile Ala Val Glu Trp Glu Ser Asn Gly Gln Pro Glu Asn
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
Fc IgG1

Asn Tyr Lys Thr Thr Pro Pro Val Leu Asp Ser Asp Gly Ser
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
Fc IgG1

Phe Phe Leu Tyr Ser Lys Leu Thr Val Asp Lys Ser Arg Trp
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
Fc IgG1

Gln Gln Gly Asn Val Phe Ser Cys Ser Val Met His Glu Ala
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
Fc IgG1

Leu His Asn His Tyr Thr Gln Lys Ser Leu Ser Leu Ser Pro
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯▶
Fc IgG1

Gly Lys
⎯⎯⎯▶
Fc IgG1

┆ : Linker / connecting sequence (if any)

Figure 10C

SEQ ID NO: 6

Phe Pro Pro Lys Pro Lys Asp Thr Leu Met Ile Ser Arg Thr
Fc IgG1

Pro Glu Val Thr Cys Val Val Val Asp Val Ser His Glu Asp
Fc IgG1

Pro Glu Val Lys Phe Asn Trp Tyr Val Asp Gly Val Glu Val
Fc IgG1

His Asn Ala Lys Thr Lys Pro Arg Glu Glu Gln Tyr Asn Ser
Fc IgG1

Thr Tyr Arg Val Val Ser Val Leu Thr Val Leu His Gln Asp
Fc IgG1

Trp Leu Asn Gly Lys Glu Tyr Lys Cys Lys Val Ser Asn Lys
Fc IgG1

Ala Leu Pro Ala Pro Ile Glu Lys Thr Ile Ser Lys Ala Lys
Fc IgG1

Gly Gln Pro Arg Glu Pro Gln Val Tyr Thr Leu Pro Pro Ser
Fc IgG1

Arg Glu Glu Met Thr Lys Asn Gln Val Ser Leu Thr Cys Leu
Fc IgG1

Val Lys Gly Phe Tyr Pro Ser Asp Ile Ala Val Glu Trp Glu
Fc IgG1

Ser Asn Gly Gln Pro Glu Asn Asn Tyr Lys Thr Thr Pro Pro
Fc IgG1

Val Leu Asp Ser Asp Gly Ser Phe Phe Leu Tyr Ser Lys Leu
Fc IgG1

Thr Val Asp Lys Ser Arg Trp Gln Gln Gly Asn Val Phe Ser
Fc IgG1

Figure 11B

SEQ ID NO: 6

Cys Ser Val Met His Glu Ala Leu His Asn His Tyr Thr Gln →
Fc IgG1

Lys Ser Leu Ser Leu Ser Pro Gly Lys →
Fc IgG1

┆ : Linker / connecting sequence (if any)

Figure 11C

SEQ ID NO: 7

Asn Lys Ala Leu Pro Ala Pro Ile Glu Lys Thr Ile Ser Lys
―――――――――――――――――――――――――――――――――――――――――――――――▶
Fc-IgG1

Ala Lys Gly Gln Pro Arg Glu Pro Gln Val Tyr Thr Leu Pro
―――――――――――――――――――――――――――――――――――――――――――――――▶
Fc-IgG1

Pro Ser Arg Glu Glu Met Thr Lys Asn Gln Val Ser Leu Thr
―――――――――――――――――――――――――――――――――――――――――――――――▶
Fc-IgG1

Cys Leu Val Lys Gly Phe Tyr Pro Ser Asp Ile Ala Val Glu
―――――――――――――――――――――――――――――――――――――――――――――――▶
Fc-IgG1

Trp Glu Ser Asn Gly Gln Pro Glu Asn Asn Tyr Lys Thr Thr
―――――――――――――――――――――――――――――――――――――――――――――――▶
Fc-IgG1

Pro Pro Val Leu Asp Ser Asp Gly Ser Phe Phe Leu Tyr Ser
―――――――――――――――――――――――――――――――――――――――――――――――▶
Fc-IgG1

Lys Leu Thr Val Asp Lys Ser Arg Trp Gln Gln Gly Asn Val
―――――――――――――――――――――――――――――――――――――――――――――――▶
Fc-IgG1

Phe Ser Cys Ser Val Met His Glu Ala Leu His Asn His Tyr
―――――――――――――――――――――――――――――――――――――――――――――――▶
Fc-IgG1

Thr Gln Lys Ser Leu Ser Leu Ser Pro Gly Lys
―――――――――――――――――――――――――――――――――――▶
Fc-IgG1

: Linker / connecting sequence (if any)

Figure 12B

SEQ ID NO: 8

Asp Val Ser His Glu Asp Pro Glu Val Lys Phe Asn Trp Tyr
Fc-IgG1

Val Asp Gly Val Glu Val His Asn Ala Lys Thr Lys Pro Arg
Fc-IgG1

Glu Glu Gln Tyr Asn Ser Thr Tyr Arg Val Val Ser Val Leu
Fc-IgG1

Thr Val Leu His Gln Asp Trp Leu Asn Gly Lys Glu Tyr Lys
Fc-IgG1

Cys Lys Val Ser Asn Lys Ala Leu Pro Ala Pro Ile Glu Lys
Fc-IgG1

Thr Ile Ser Lys Ala Lys Gly Gln Pro Arg Glu Pro Gln Val
Fc-IgG1

Tyr Thr Leu Pro Pro Ser Arg Glu Glu Met Thr Lys Asn Gln
Fc-IgG1

Val Ser Leu Thr Cys Leu Val Lys Gly Phe Tyr Pro Ser Asp
Fc-IgG1

Ile Ala Val Glu Trp Glu Ser Asn Gly Gln Pro Glu Asn Asn
Fc-IgG1

Tyr Lys Thr Thr Pro Pro Val Leu Asp Ser Asp Gly Ser Phe
Fc-IgG1

Phe Leu Tyr Ser Lys Leu Thr Val Asp Lys Ser Arg Trp Gln
Fc-IgG1

Gln Gly Asn Val Phe Ser Cys Ser Val Met His Glu Ala Leu
Fc-IgG1

His Asn His Tyr Thr Gln Lys Ser Leu Ser Leu Ser Pro Gly
Fc-IgG1

Figure 13B

SEQ ID NO: 8

: Linker / connecting sequence (if any)

SEQ ID NO: 9

Fusion polypeptide sequence of ETBR ligand-binding domains

| N terminus+ ICL1 | Fc IgG1 |
|---|---|
| Pro93 → Cys131 | Lys105 → Lys330 |

Pro Ile Glu Ile Lys Glu Thr Phe Lys Tyr Ile Asn Thr Val
———————————————————————————————→
ETBR

Val Ser Cys Leu Val Phe Val Leu Gly Ile Ile Gly Asn Ser
———————————————————————————————→
ETBR

Thr Leu Leu Arg Ile Ile Tyr Lys Asn Lys Cys | Lys Thr His
—————————————————————————————→ ——————→
ETBR                                          Fc-IgG1

Thr Cys Pro Pro Cys Pro Ala Pro Glu Leu Leu Gly Gly Pro
———————————————————————————————→
Fc-IgG1

Ser Val Phe Leu Phe Pro Pro Lys Pro Lys Asp Thr Leu Met
———————————————————————————————→
Fc-IgG1

Ile Ser Arg Thr Pro Glu Val Thr Cys Val Val Val Asp Val
———————————————————————————————→
Fc-IgG1

Ser His Glu Asp Pro Glu Val Lys Phe Asn Trp Tyr Val Asp
———————————————————————————————→
Fc-IgG1

Gly Val Glu Val His Asn Ala Lys Thr Lys Pro Arg Glu Glu
———————————————————————————————→
Fc-IgG1

Gln Tyr Asn Ser Thr Tyr Arg Val Val Ser Val Leu Thr Val
———————————————————————————————→
Fc-IgG1

Leu His Gln Asp Trp Leu Asn Gly Lys Glu Tyr Lys Cys Lys
———————————————————————————————→
Fc-IgG1

Val Ser Asn Lys Ala Leu Pro Ala Pro Ile Glu Lys Thr Ile
———————————————————————————————→
Fc-IgG1

Figure 14A

SEQ ID NO: 9

Ser Lys Ala Lys Gly Gln Pro Arg Glu Pro Gln Val Tyr Thr
―――――――――――――――――――――――――――――――――――――――――――――▶
Fc- IgG1

Leu Pro Pro Ser Arg Glu Glu Met Thr Lys Asn Gln Val Ser
―――――――――――――――――――――――――――――――――――――――――――――▶
Fc- IgG1

Leu Thr Cys Leu Val Lys Gly Phe Tyr Pro Ser Asp Ile Ala
―――――――――――――――――――――――――――――――――――――――――――――▶
Fc- IgG1

Val Glu Trp Glu Ser Asn Gly Gln Pro Glu Asn Asn Tyr Lys
―――――――――――――――――――――――――――――――――――――――――――――▶
Fc- IgG1

Thr Thr Pro Pro Val Leu Asp Ser Asp Gly Ser Phe Phe Leu
―――――――――――――――――――――――――――――――――――――――――――――▶
Fc- IgG1

Tyr Ser Lys Leu Thr Val Asp Lys Ser Arg Trp Gln Gln Gly
―――――――――――――――――――――――――――――――――――――――――――――▶
Fc- IgG1

Asn Val Phe Ser Cys Ser Val Met His Glu Ala Leu His Asn
―――――――――――――――――――――――――――――――――――――――――――――▶
Fc- IgG1

His Tyr Thr Gln Lys Ser Leu Ser Leu Ser Pro Gly Lys
―――――――――――――――――――――――――――――――――――――――――▶
Fc- IgG1

⋮ : Linker / Connecting sequence (if any)

Figure 14B

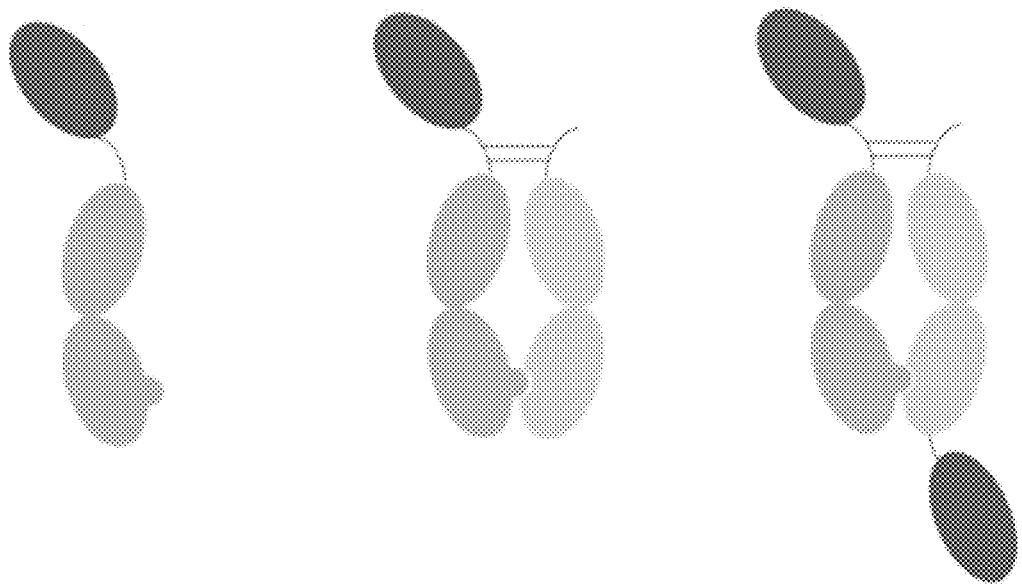

ENDOTHELIN-1 RECEPTOR BASED ENDOTHELIN-1 SPONGE

CROSS-REFERENCE TO RELATED APPLICATIONS

The present application is a continuation-in-part of international application no. PCT/IB2016/050337, filed Jan. 22, 2016, insofar as it designates the United States. The entire contents of this international application are hereby incorporated herein by reference.

The Sequence Listing in ASCII text file format of 32,748 bytes in size, created on May 14, 2020, with the file name "2020-05-14SequenceListing_JAIN1," filed in the U.S. Patent and Trademark Office on even date herewith, is hereby incorporated herein by reference.

DESCRIPTION OF THE INVENTION

Background

Endothelin-1 is a vasoactive peptide synthesized and secreted by a diverse range of cells, and thus implicated in signalling events in a wide variety of target tissues (Nelson et al. 2003). Endothelin-1 plays a key role in physiological functions. However, under elevated levels, endothelin-1 induces pathology and as such is implicated in a host of different diseases, including neurodegenerative disorders, cardiovascular diseases, as well as pregnancy disorders like preeclampsia (Jain 2013, Jain et al. 2012). Given that a key feature of these diseases is elevated endothelin-1 levels, one proposed strategy of therapeutic intervention is targeting the increased levels of endothelin-1. To this end, fusion polypeptides capable of binding endothelin-1 to form a nonfunctional complex would serve as endothelin-1 antagonists. The construction of these endothelin-1 antagonists, termed endothelin-1 sponge, would require fusing the endothelin-1 receptor(s) ligand-binding domains to the Fc portion of human IgG 1. The structure of such constructs is shown in FIGS. 18A-C, in which the darkest ovals represent the endothelin-1 receptor and the remaining ovals represent either the monomeric or dimeric Fc portions of human IgG1.

Endothelin-1 exerts its effects by binding to the endothelin A (ETA) and endothelin B (ETB) receptors, two highly homologous cell-surface proteins that belong to the G-protein-coupled receptor superfamily (Karet and Davenport 1994). The two receptors share about 60% similarity in the primary structure (Nelson et al. 2003), i.e. both receptors exhibit a high polypeptide sequence identity with each other. Nevertheless, the two receptors show a clear distinction in ligand binding selectivity based on their ligand-binding domains.

Endothelin-1 Binding to the ETA Receptor:

Endothelin-1 binding to the ETA receptor is thought to require the ETA receptor N-terminus loop, extracellular loop 1 (ECL1), extracellular loop 2 (ECL2), intracellular loop 3 (ICL3), extracellular loop 3 (ECL3) and the C-terminal domain (Adachi et al. 1993). Amino acid sequences of these ETA receptor ligand-binding domains are given in FIG. 1.

A five amino acid sequence (140-Lys Leu Leu Ala Gly-144) (residues 61-65 of SEQ ID NO:1) in ECL1 has been implicated as the most important element required for ligand binding. In addition, both ECL2 and ECL3, including the flanking transmembrane regions, were found to play an important role in ligand selection.

Orry et al. (2000) also constructed a model of interaction of the ET-1 peptide with the ETA receptor, where ET-1 makes contacts with both the N-terminal receptor domain and two different extracellular loops.

Further, the C-terminal eight amino acid residues located in close proximity to the seventh transmembrane region and the C-terminal 16 amino acid residues in the third intracellular loop are important for endothelin-1 binding (Adachi et al. 1993).

Endothelin-1 Binding to the ETB Receptor:

Endothelin-1 binding to the ETB receptor requires the 39 amino acids between Pro93 in the N-terminal domain and Cys131 in the first intracellular loop of the ETB receptor (Klammt et al. 2007). In addition, the 12 amino acids from Ser390 to Leu401 in the proximal cytoplasmic tail are necessary to maintain the ligand-binding site in an active form (Wada et al. 1995).

Further, it has been suggested that the 60 amino acid sequence from Ile138 to Ile197 located in transmembrane domains 2 and 3 (TM2+3) might also be important for ligand binding. Amino acid sequences of these ETB receptor ligand-binding domains are given in FIG. 2.

Constructing Endothelin-1 Sponge:

1. Endothelin-1 sponge could be constructed by fusing the above mentioned ETA receptor ligand-binding domains into a fusion polypeptide that can then be fused to the Fc portion of human IgG1 (FIG. 3).

2. Endothelin-1 sponge could be constructed by fusing the above mentioned ETB receptor ligand-binding domains into a fusion polypeptide that can then be fused to the Fc portion of human IgG1 (FIG. 4).

3. Endothelin-1 sponge could be constructed by fusing the ETB receptor ligand-binding domains inline with the ETA receptor ligand-binding domains into a fusion polypeptide that can then be fused to the Fc portion of human IgG1 (FIG. 5).

The present invention provides amino acid sequences of fusion polypeptides capable of binding endothelin-1 to form a nonfunctional complex comprising:

a) ETA receptor ligand-binding domains and/or b) ETB receptor ligand-binding domains fused to the Fc portion of human IgG1.

SUMMARY OF THE INVENTION

An object of the present invention is the production of endothelin-1 antagonists that are useful in the treatment of endothelin-1-related diseases or disorders.

Another object of the invention is the use of the disclosed endothelin-1 antagonists for the treatment of endothelin-1-related diseases or disorders. For example, an endothelin-1 antagonist described herein may be used for the treatment of preeclampsia, cardiovascular diseases, diabetes or neurodegenerative disorders, which are all conditions where endothelin-1 levels are pathologically elevated (Zeiher et al., 1995; Seligman et al., 2000; Schneider et al., 2002; Haufschild et al., 2001; Pache et al., 2003; Sethi et al., 2006; Jain et al., 2012).

Another object of the invention is the construction of several specific endothelin-1 antagonists, termed endothelin-1 sponge, each having different sequences but all being capable of blocking the binding of endothelin-1 to its receptor(s), thus functioning as endothelin-1 antagonists.

DESCRIPTION OF THE FIGURES

FIG. 1. ETA receptor ligand-binding domains. N terminus is residues 1-60 of SEQ ID NO:1; Extracellular loop 1 is residues 61-79 of SEQ ID NO:1; Extracellular loop 2 is residues 80-108 of SEQ ID NO:1; Extracellular loop 3 is residues 141-156 of SEQ ID NO:1; Intracellular loop 3 is residues 109-140 of SEQ ID NO:1; and C terminus is residues 157-211 of SEQ ID NO:1.

FIG. 2. ETB receptor ligand-binding domains. N terminus+ Intracellular loop 1 is residues 1-39 of SEQ ID NO:7; C terminus is residues 40-51 of SEQ ID NO:7; and Transmembrane domains 2+3 is residues 40-99 of SEQ ID NO:8.

FIG. 6A-C. SEQ ID NO: 1, comprising ETA receptor (ETAR) ligand-binding domains, including the N-terminus, ECL1, ECL2, ICL3, ECL3 and C-terminus, fused to the Fc portion of human IgG1.

FIG. 7A-C. SEQ ID NO: 2, comprising ETA receptor (ETAR) ligand-binding domains, including the N-terminus, ECL1, ECL2, ICL3 (16 amino acids), ECL3 and C-terminus (8 amino acids), fused to the Fc portion of human IgG1.

FIG. 8A-C. SEQ ID NO: 3, comprising ETA receptor (ETAR) ligand-binding domains, including the N-terminus, ECL1, ECL2, ICL3 and C-terminus, fused to the Fc portion of human IgG1.

FIG. 9A-C. SEQ ID NO: 4, comprising ETA receptor (ETAR) ligand-binding domains, including the N-terminus, ECL1, ECL2, ICL3 (16 amino acids) and C-terminus (8 amino acids), fused to the Fc portion of human IgG1.

FIG. 10A-C. SEQ ID NO: 5, comprising ETA receptor (ETAR) ligand-binding domains, including the N-terminus, ECL1, ICL3, ECL3 and C-terminus, fused to the Fc portion of human IgG1.

FIG. 11A-C. SEQ ID NO: 6, comprising ETA receptor (ETAR) ligand-binding domains, including the N-terminus, ECL1, ICL3 (16 amino acids), ECL3 and C-terminus (8 amino acids), fused to the Fc portion of human IgG1.

FIG. 12A-B. SEQ ID NO: 7, comprising ETB receptor (ETBR) ligand-binding domains, including the N-terminus, ICL1 and C-terminus, fused to the Fc portion of human IgG 1.

FIG. 13A-C. SEQ ID NO: 8, comprising ETB receptor (ETBR) ligand-binding domains, including the N-terminus, ICL1, TM2+3 and C-terminus, fused to the Fc portion of human IgG1.

FIG. 14A-B. SEQ ID NO: 9, comprising ETB receptor (ETBR) ligand-binding domains, including the N-terminus and ICL1, fused to the Fc portion of human IgG1.

FIG. 18A-C shows possible formats of Fc-fusion constructs. FIG. 18A shows monomeric Fc, while FIGS. 18B and 18C show different structures of heterodimeric Fc (Jain et al. 2017).

DETAILED DESCRIPTION

Figure 3:
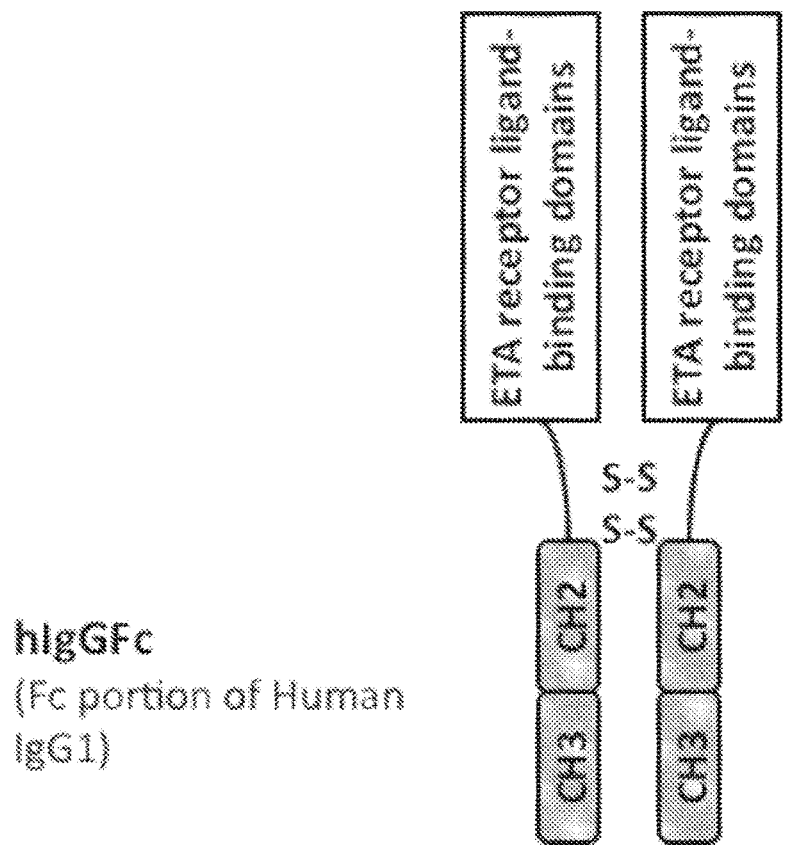
FIG. 3. Proposed design of ET-1 sponge based on ETA receptor ligand-binding domains.
Figure 4:
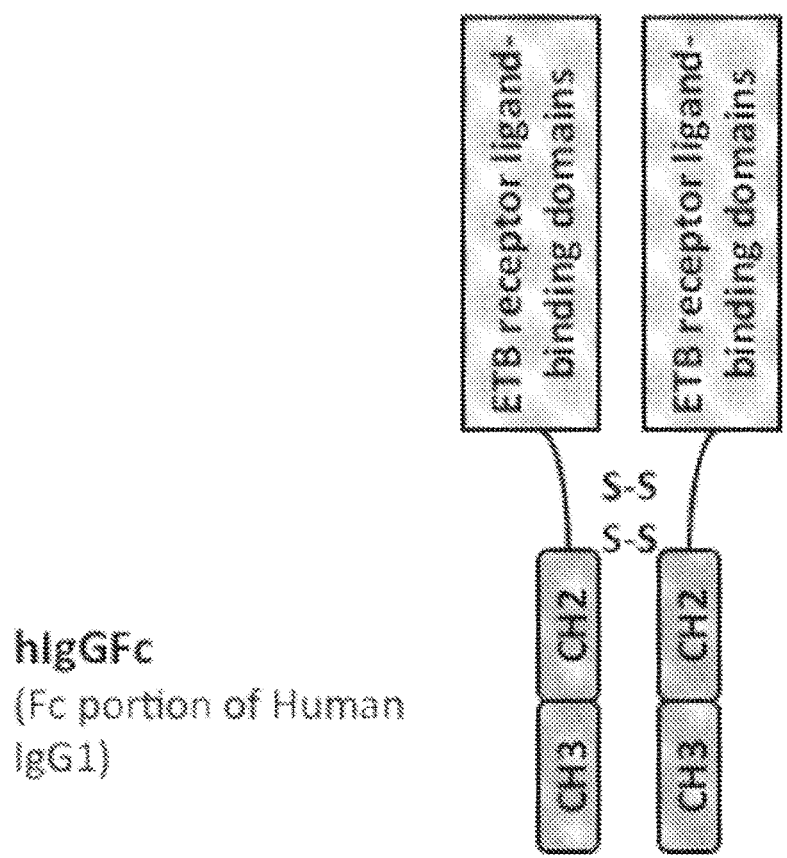
FIG. 4. Proposed design of ET-1 sponge based on ETB receptor ligand-binding domains.
Figure 5:
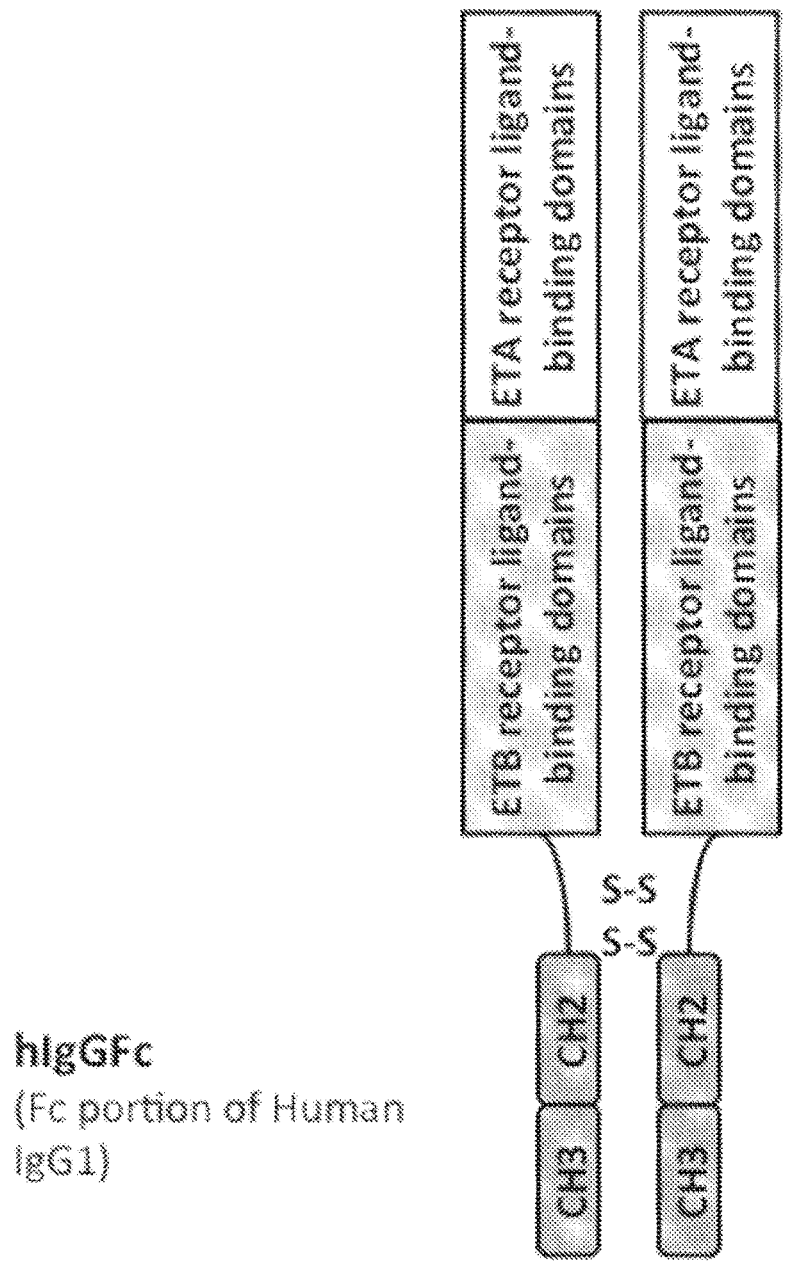
FIG. 5. Proposed design of ET-1 sponge based on ETA and ETB receptors' ligand-binding domains.
Figure 6A:
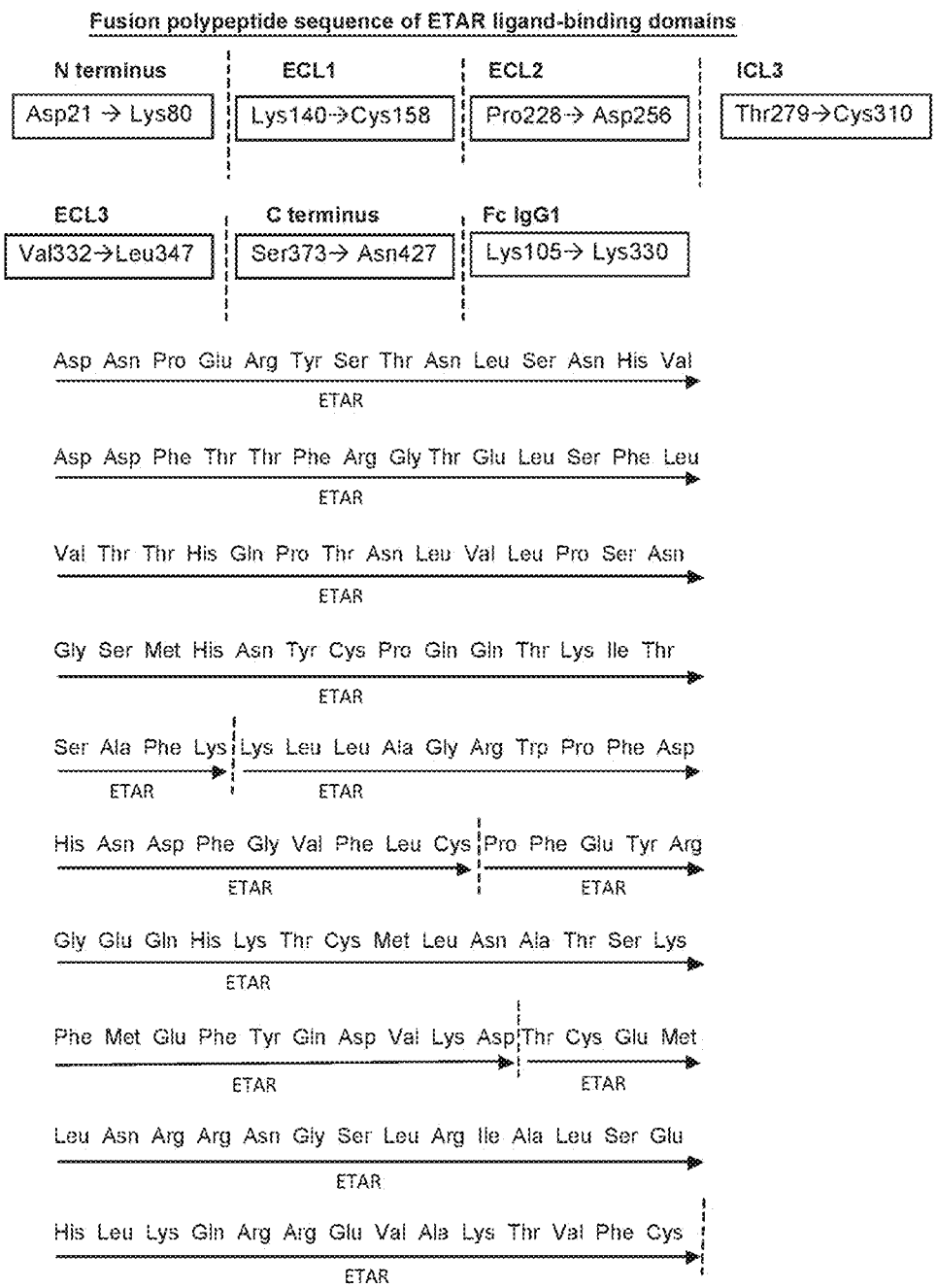
Figure 7A:
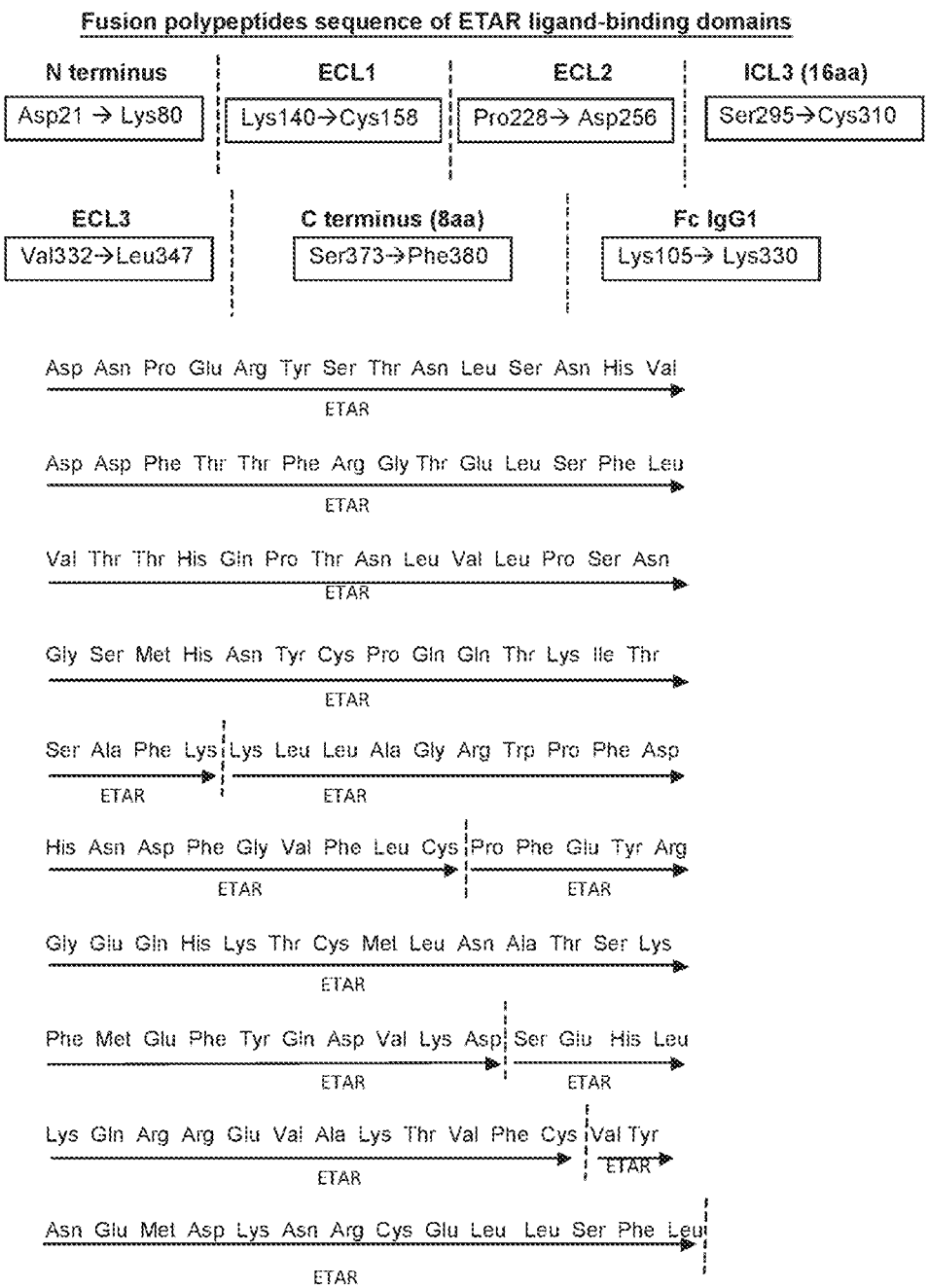
Figure 7B:
Figure 8A:
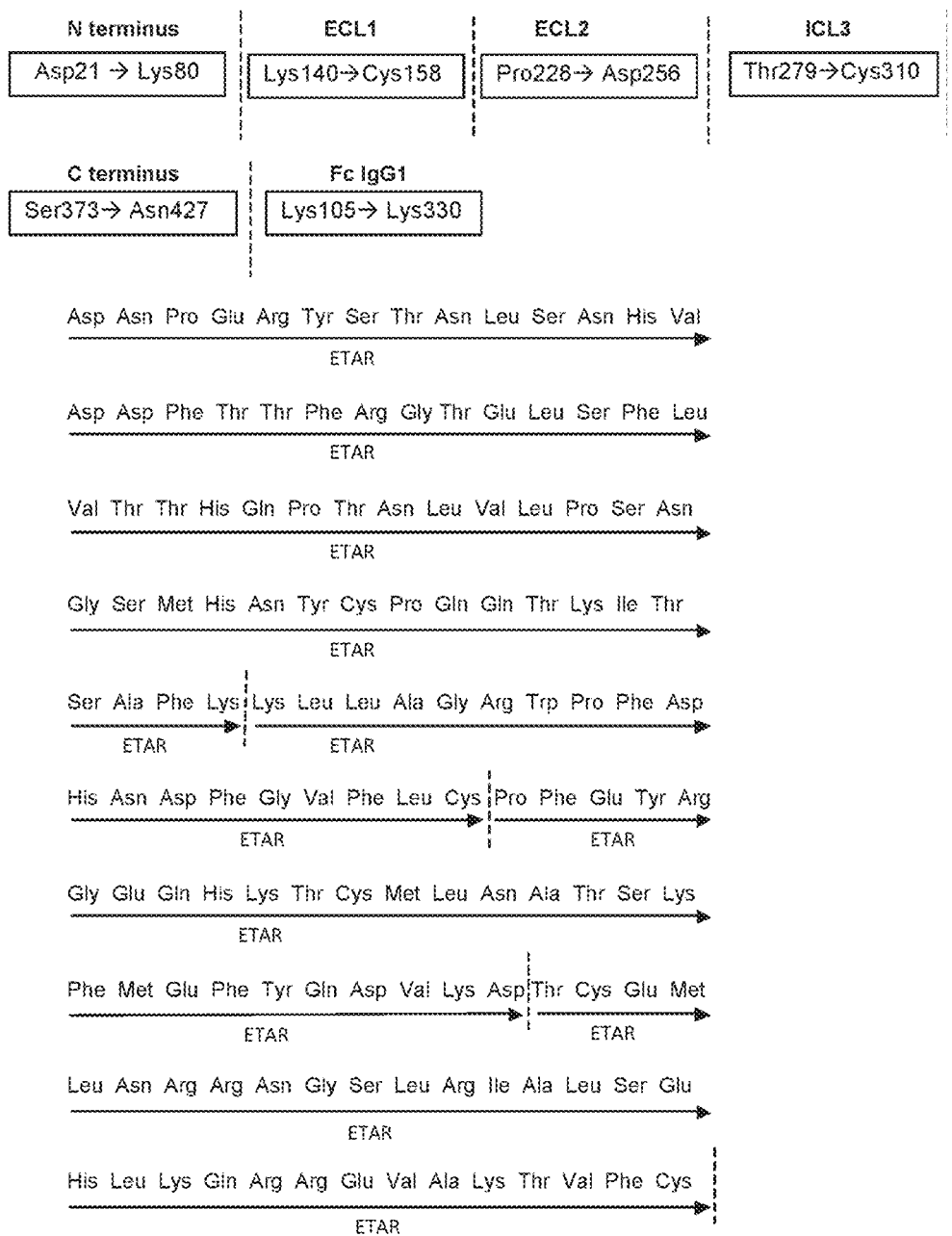
Figure 9A:
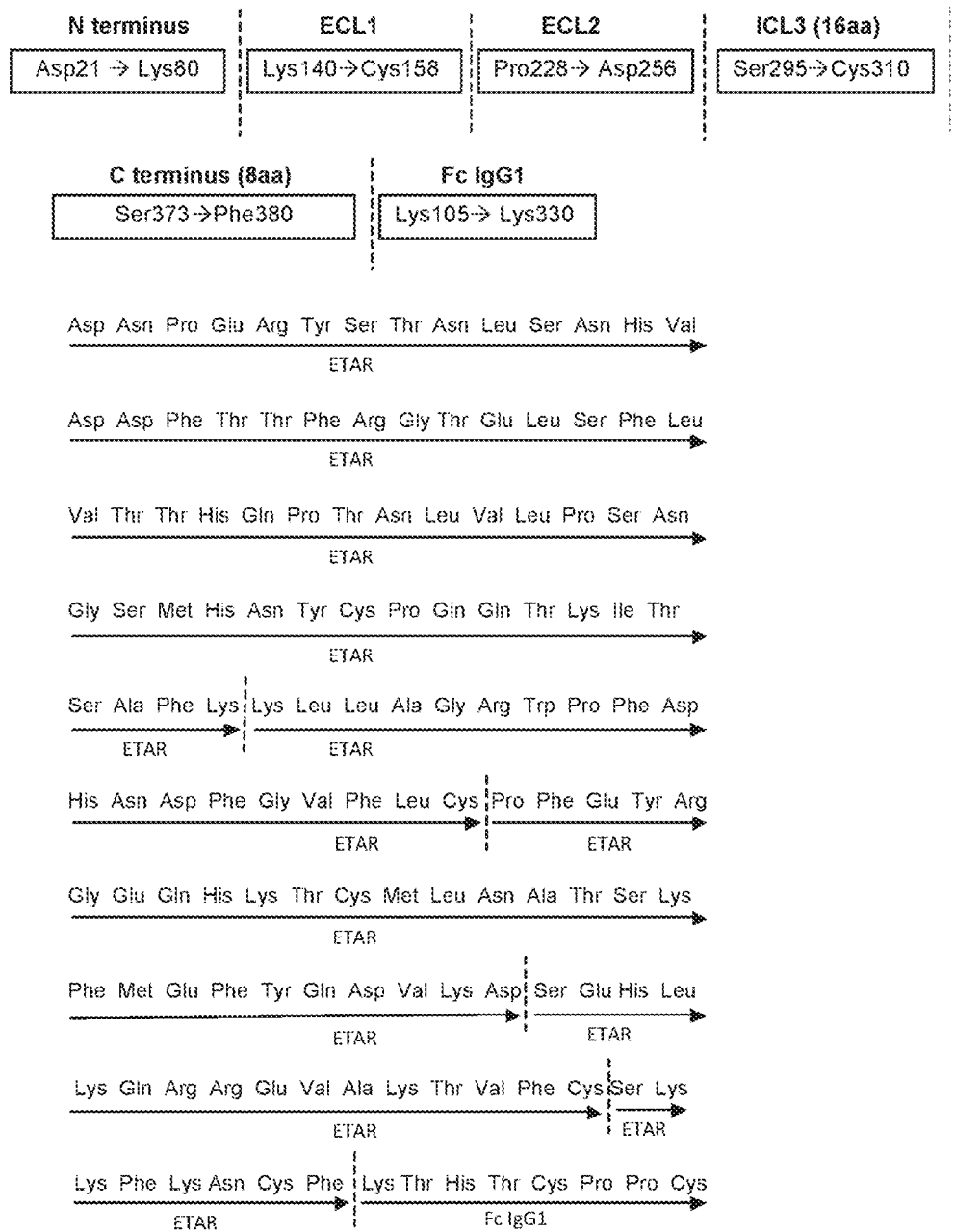
Figure 10A:
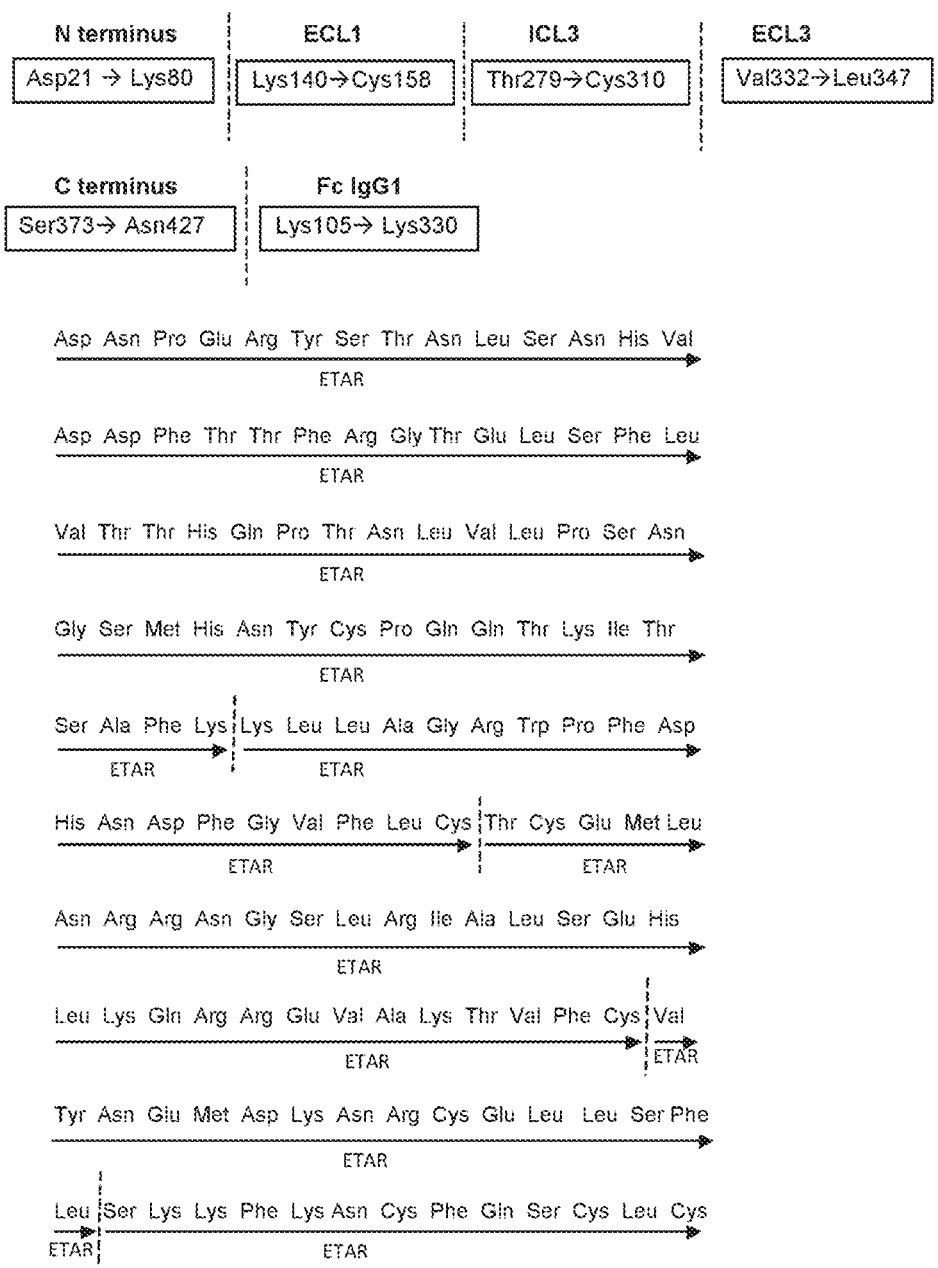
Figure 11A:
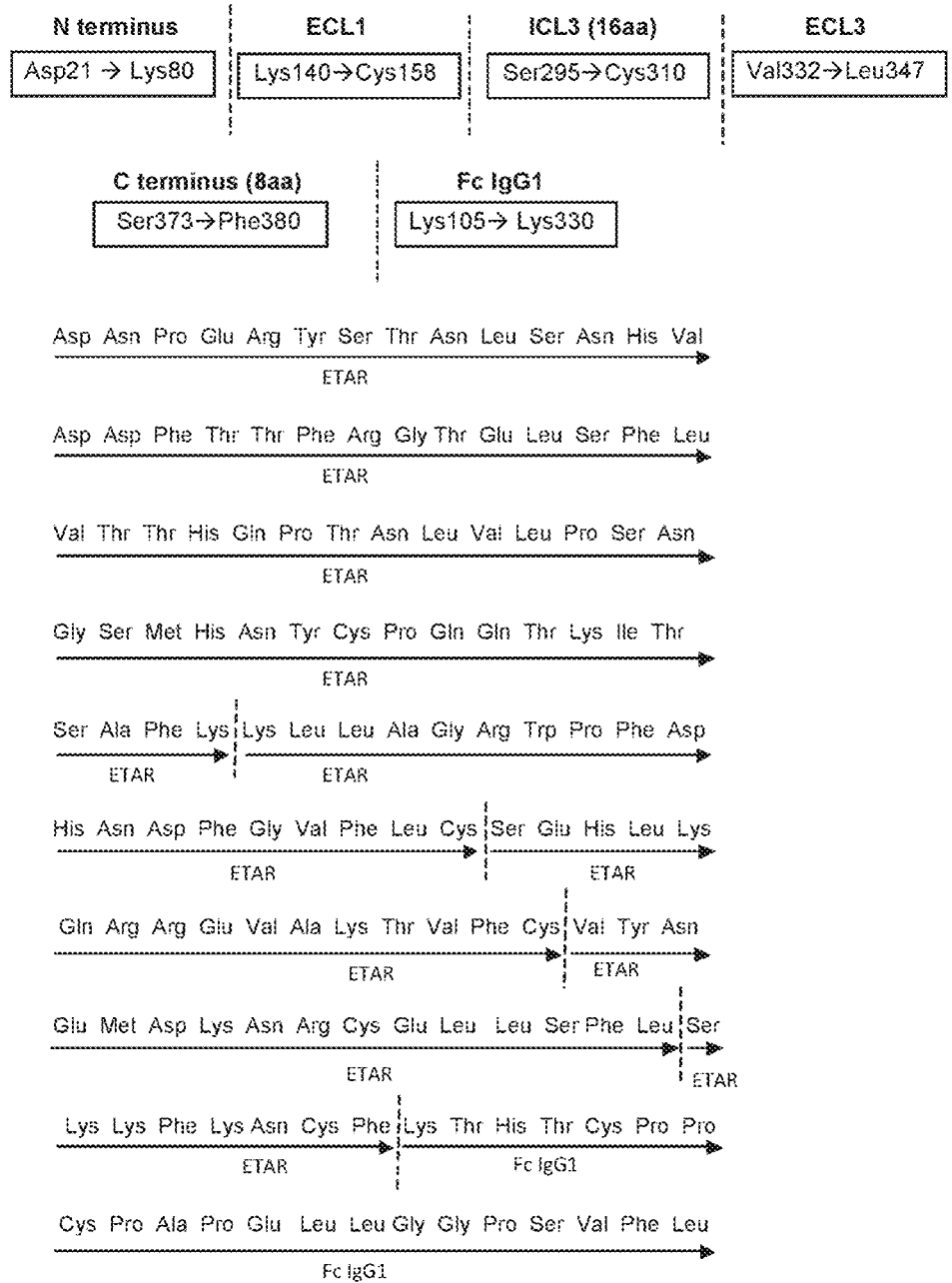
Figure 12A:
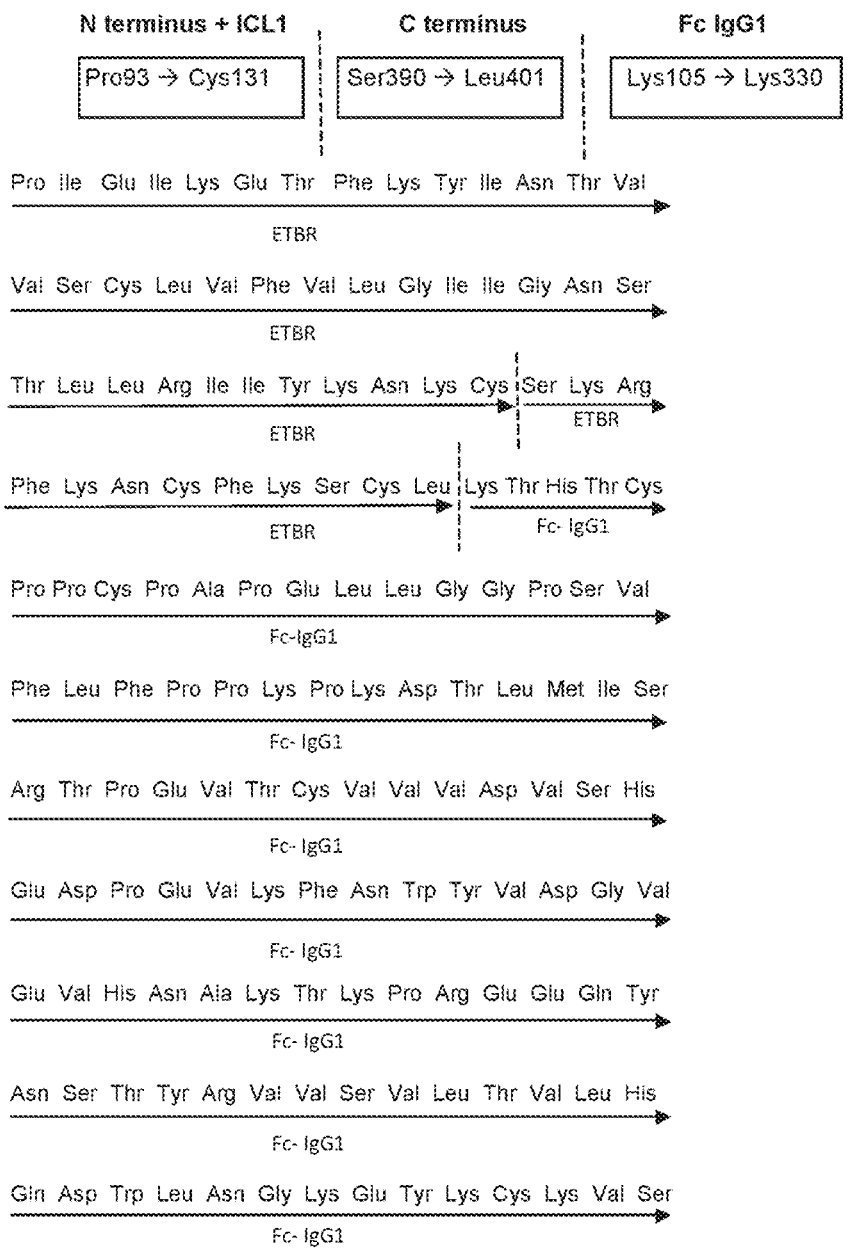
Figure 13A:
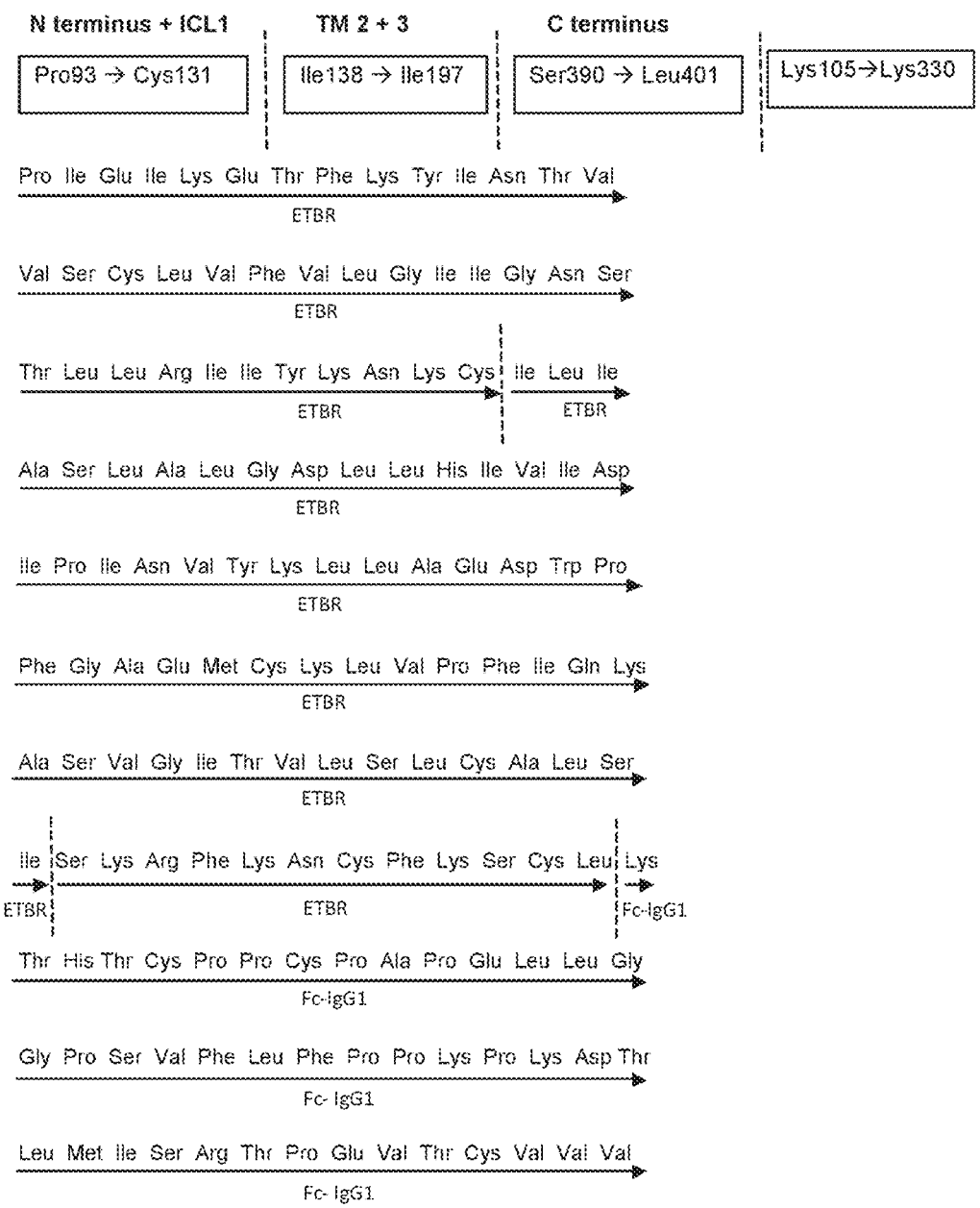
Figure 13C:
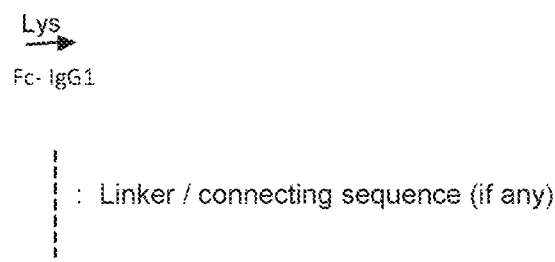

The invention relates to fusion polypeptides, i.e. polypeptides comprising various domains of the ETA/ETB receptor. A polypeptide, as used in the context of the present invention, is typically a single linear polymer chain of amino acids bonded together by peptide bonds between the carboxyl and amino groups of adjacent amino acid residues. The term "protein" may also be used to describe a large polypeptide. The term "protein" is meant to include quaternary structures, ternary structures and other complex macromolecules composed of at least one polypeptide.

The fusion polypeptides of the present invention are capable of binding to endothelin-1 to form a non-functional complex. Standard methods in the art, such as surface plasmon resonance, may be used to determine whether a fusion polypeptide is capable of binding to endothelin-1.

In the context of the present invention, a "non-functional complex" means a complex where the endothelin-1 bound to the fusion polypeptide is sequestered and prevented from activating its signalling pathway (in other words, the fusion polypeptides are antagonistic). The ETA and ETB receptors are coupled to a G-protein and binding of endothelin-1 to its receptors, e.g., in smooth muscle, promotes the formation of $IP_3$. Increased $IP_3$ causes calcium release by the sarcoplasmic reticulum and causes smooth muscle contraction. ETB receptors are also found on the endothelium and binding of ET-1 stimulates formation of nitric oxide.

The skilled person would readily be able to test for formation of a non-functional complex, for example, using calcium mobilisation assays and cell lines expressing ETA/ETB. Such procedures are well known in the art and may use a calcium-sensitive dye and fluorescence imaging (see for example Wang et al (2016), Int J Mol Sci, 17(3):389. doi: 10.3390/ijms17030389, which discloses in vitro assays for ETA/ETB activity).

In some instances, the various ET receptor domains making up the fusion polypeptide may be contiguous. In other instances, linker sequences may be used to join the domains. Such linkers are discussed further below.

In some instances, the fusion polypeptide is fused to an Fc domain, typically to the Fc portion of human IgG1. The term "Fc" typically refers to a portion of a heavy chain constant region that comprises at least the CH2 and CH3 domains that typically bind to an Fc receptor, e.g., an FcγR, namely FcγRI (CD64), FcγRII (CD32), FcγRIII (CD16) or an FcRn, i.e., a neonatal Fc receptor. If the CH2 and CH3 region contains deletions, substitutions, and/or insertions or other modifications that render it unable to bind any Fc receptor, then the CH2 and CH3 region is considered to be non-functional in terms of its typical biological function.

The phrase "fused to", as used herein, may mean (but is not limited to) a polypeptide formed by expression of a chimeric gene made by combining more than one sequence, typically by cloning one gene into an expression vector in frame with a second gene such that the two genes are encoding one continuous polypeptide. In addition to being made by recombinant technology, parts of a polypeptide can be "fused to" each other by means of chemical reaction, or other means known in the art for making custom polypeptides.

Methods of making fusion proteins are known in the art. In one such method, a DNA expression vector would be engineered to contain an ETA/ETB receptor ligand binding domain-encoding nucleic acid sequence linked in-frame to an Fc-encoding nucleic acid sequence such that the DNA expression vector expresses one contiguous fusion polypeptide. The ETA/ETB receptor ligand binding domains may be linked to the C-terminus or to the N-terminus of the Fc-containing polypeptide. FIG. 18C shows a heterodimeric Fc structure with both types of fusions.

In the context of constructing fusion proteins, the phrase "joined in-frame" means that the components are linked together is such a way that their complete translation, use or operation is possible and thus not disrupted. For example, a fusion protein comprising at least two polypeptides, may or may not have a linker or spacer sequence between the polypeptides, and thus the polypeptides are joined in-frame as one continuous polypeptide with each polypeptide maintaining its operability. Two or more polypeptides linked or fused together in a fusion protein are typically derived from two or more independent sources, and therefore a fusion protein comprises two or more linked polypeptides not normally found linked in nature. Furthermore, DNA encoding such fusion proteins may contain linker sequences that maintain operable in-frame (e.g., triplet codon) translation of the transcribed mRNA molecules encoding such polypeptides.

The phrase "operably linked", such as in the context of DNA expression vector constructs, a control sequence, e.g., a promoter or operator, is appropriately placed at a position relative to a coding sequence such that the control sequence directs the production of a polypeptide encoded by the coding sequence.

In some instances, the components of an (Fc-) fusion protein are separated by a linker (or "spacer") peptide. Such peptide linkers are well known in the art (e.g., polyglycine) and typically allow for proper folding of one or both of the polypeptides. The linker provides a flexible junction region, allowing the two ends of the molecule to move independently, and may play an important role in retaining each of the two moieties' appropriate functions. Therefore, the junction region acts in some cases as both a linker, which combines the two parts together, and as a spacer, which allows each of the two parts to form its own biological structure and not interfere with the other part. Furthermore, the junction region should create an epitope that will not be recognized by the subject's immune system as foreign, in other words, will not be considered immunogenic. Linker selection may also have an effect on binding activity of the fusion molecule. (See Huston, et al, 1988, *PNAS*, 85: 16: 5879-83; Robinson & Bates, 1998, *PNAS* 95(11): 5929-34; Arai, et al. 2001, *PEDS*, 14(8): 529-32; and Chen, X. et al., 2013, *Advanced Drug Delivery Reviews* 65: 1357-1369.) In one instance, the ETA/ETB receptor ligand-binding domains are connected to the C-terminus or to the N-terminus of the Fc-containing polypeptide, or fragment thereof, via one or more peptide linkers.

The length of the linker chain may be 2, 3, 4, 5, 6, 7, 8, 9, 10, 11, 12, 13, 14 15 or more amino acid residues, but typically is between 5 and 25 residues. Examples of linkers include polyGlycine linkers, such as Gly-Gly, Gly-Gly-Gly (3Gly), 4Gly (SEQ ID NO:10, where residues 5-9 are absent), 5Gly (SEQ ID NO:10, where residues 6-9 are absent), 6Gly (SEQ ID NO:10, where residues 7-9 are absent), 7Gly (SEQ ID NO:10, where residues 8-9 are absent), 8Gly (SEQ ID NO:10, where residues 9 is absent) or 9Gly (SEQ ID NO:10, where residues 1-9 are present). Examples of linkers also include Gly-Ser peptide linkers such as Ser-Gly, Gly-Ser, Gly-Gly-Ser, Ser-Gly-Gly, Gly-Gly-Gly-Ser (residues 3-6 of SEQ ID NO:12), Ser-Gly-Gly-Gly (residues 1-4 of SEQ ID NO:11), Gly-Gly-Gly-Gly-Ser (residues 2-6 of SEQ ID NO:12), Ser-Gly-Gly-Gly-Gly (SEQ ID NO:11), Gly-Gly-Gly-Gly-Gly-Ser (SEQ ID NO:12), Ser-Gly-Gly-Gly-Gly-Gly-Gly (SEQ ID NO:15), Gly-Gly-Gly-Gly-Gly-Gly-Ser (SEQ ID NO:16), Ser-Gly-Gly-Gly-Gly-Gly-Gly-Gly (SEQ ID NO:17), (Gly-Gly-Gly-Gly-Ser)n (SEQ ID NO:13), and (Ser-Gly-Gly-Gly-Gly)n (SEQ ID NO:14), wherein n=1 to 10. (Gly-Gly-Gly-Gly-Ser)n (SEQ ID NO:13) and (Ser-Gly-Gly-Gly-Gly)n (SEQ ID NO:14) are also known as (G4S)n and (S4G)n, respectively. In no case will such a linker sequence include the naturally occurring sequence between the polypeptide segments in the natural receptors, which natural sequences are explicity excluded from the definition of "linker sequence."

In some instances, the fusion polypeptide of the present invention is monomeric, such as is illustrated in FIG. 18A. Such a monomeric fusion protein may be useful as an intermediate in the formation of a therapeutically active multimer, or such a monomeric fusion protein may be therapeutically active on its own. The fusion polypeptide may also be capable of forming a multimer, particularly a dimer, such as is illustrated in FIGS. 18B and 18C. The invention therefore also provides a multimer of the fusion polypeptide, optionally wherein the multimer is a dimer.

Multimerisation of such ligand traps is known in the art (see for example WO 00/75319). In order for multimerisation to occur, a multimerisation component is typically present which allows formation of a complex comprising multiple (i.e., more than one) of the fusion polypeptide. A multimerisation component can be any macromolecule (i.e. protein, polypeptide, peptide) that has the ability to associate with a second multimerisation component of the same or a similar structure. Multimerisation may involve an amino acid sequence comprising a cysteine residue, which allows the formation of disulphide bonds. Multimerisation components can also be leucine zippers, a helix-loop motif, a coiled-coil motif or an immunoglobulin derived domain (for example, a CH3 domain). Typically, an Fc domain (as discussed above) acts as a multimerisation component. The Fc domain may be from IgG1, IgG2, IgG3 or IgG4, but is preferably from IgG1.

Expression vectors may be used for recombinant production of polypeptides of the invention. An expression vector in the context of the present invention may be any suitable vector, including chromosomal, non-chromosomal, and synthetic nucleic acid vectors (a nucleic acid sequence comprising a suitable set of expression control elements).

Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, an Fc-fusion protein or polypeptide-encoding nucleic acid molecule is comprised in a naked DNA or RNA vector, including, for example, a linear expression element, a compacted nucleic acid vector (as described in, for instance, U.S. Pat. No. 6,077,835 and/or WO 00/70087), or a plasmid vector such as pBR322, pUC 19/18, or pUC 118/119. Such nucleic acid vectors and the usage thereof are well known in the art (see, for instance, U.S. Pat. Nos. 5,589,466 and 5,973,972).

The vector may comprise a nucleic acid molecule encoding a polypeptide of the invention, including an expression vector comprising the nucleic acid molecules described wherein the nucleic acid molecule is operatively linked to an expression control sequence. The vector may be suitable for expression of a polypeptide in a bacterial cell. Examples of such vectors include expression vectors such as BlueScript (Stratagene), pIN vectors (Van Heeke & Schuster, 1989, *J Biol Chem* 264, 5503-5509), pET vectors (Novagen, Madison, Wis.) and the like.

An expression vector may also or alternatively be a vector suitable for expression in a yeast system. Any vector suitable for expression in a yeast system may be employed. Suitable vectors include, for example, vectors comprising constitutive or inducible promoters such as yeast alpha factor, alcohol oxidase and PGH.

The expression vector may also be suitable for expression in baculovirus-infected insect cells (Kost, T; and Condreay, J P, 1999, "Current Opinion in Biotechnology" 10 (5): 428-33).

A vector comprising a nucleic acid molecule may be provided, wherein the nucleic acid molecule is operably linked to an expression control sequence suitable for expression in a mammalian host cell.

Expression control sequences are engineered to control and drive the transcription of genes of interest, and subsequent expression of proteins in various cell systems. Plasmids combine an expressible gene of interest with expression control sequences (i.e., expression cassettes) that comprise desirable elements such as, for example, promoters, enhancers, selectable markers, operators, etc. In an expression vector of the invention, the fusion polypeptide may comprise or be associated with any suitable promoter, enhancer, selectable marker, operator, repressor protein, polyA termination sequences and other expression-facilitating elements. Examples of such elements include strong expression promoters (e.g., human CMV IE promoter/enhancer or CMV major IE (CMV-MIE) promoter, as well as RSV, SV40 late promoter, SL3-3, MMTV, ubiquitin (Ubi), ubiquitin C (UbC), and HIV LTR promoters).

Nucleic acid molecules of the invention may also be operably linked to an effective poly (A) termination sequence, an origin of replication for plasmid product in *E. coli*, an antibiotic resistance gene as selectable marker, and/or a convenient cloning site (e.g., a polylinker). Nucleic acids may also comprise a regulatable inducible promoter (inducible, repressable, developmentally regulated) as opposed to a constitutive promoter such as CMV IE (the skilled artisan will recognize that such terms are actually descriptors of a degree of gene expression under certain conditions). Selectable markers are elements well-known in the art. Under the selective conditions, only cells that express the appropriate selectable marker can survive. Commonly, selectable marker genes express proteins, usually enzymes, that confer resistance to various antibiotics in cell culture. In other selective conditions, cells that express a fluorescent protein marker are made visible, and are thus selectable. Embodiments include beta-lactamase (bla) (beta-lactam antibiotic resistance or ampicillin resistance gene or ampR), bls (blasticidin resistance acetyl transferase gene), bsd (blasticidin-S deaminase resistance gene), bsr (blasticidin-S resistance gene), Sh ble (Zeocin® resistance gene), hygromycin phosphotransferase (hpt) (hygromycin resistance gene), tetM (tetracycline resistance gene or tetR), neomycin phosphotransferase II (npt) (neomycin resistance gene or neoR), kanR (kanamycin resistance gene), and pac (puromycin resistance gene).

"Operator" may indicate a DNA sequence that is introduced in or near a gene in such a way that the gene may be regulated by the binding of the RFP to the operator and, as a result, prevents or allow transcription of the gene of interest, i.e., a nucleotide encoding a polypeptide of the invention. A number of operators in prokaryotic cells and bacteriophage have been well characterized. These include, but are not limited to, the operator region of the LexA gene of *E. coli*, which binds the LexA peptide, and the lactose and tryptophan operators, which bind the repressor proteins encoded by the LacI and trpR genes of *E. coli*. These also include the bacteriophage operators from the lambda PR and the phage P22 ant/mnt genes, which bind the repressor proteins encoded by lambda cI and P22 arc.

The term "cell" includes any cell that is suitable for expressing a recombinant nucleic acid sequence. Cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. partoris, P. methanolica*, etc.), plant cells, insect cells (e.g. SF-9, SF-21, baculovirus-infected insect cells, *Trichoplusia ni*, etc.), non-human animal cells, mammalian cells, human cells, or cell fusions such as, for example, hybridomas or quadromas. The cell may be a human, monkey, ape, hamster, rat or mouse cell. The cell may also be eukaryotic and is selected from the following cells: CHO (e.g. CHO K1, DXB-11 CHO, Veggie-CHO), COS (e.g. COS-7), retinal cells, Vero, CV1, kidney (e.g. HEK293, 293 EBNA, MSR 293, MDCK, HaK, BHK21), HeLa, HepG2, WI38, MRC 5, Colo25, HB 8065, HL-60, Jurkat, Daudi, A431 (epidermal), CV-1, U937, 3T3, L cell, C127 cell, SP2/0, NS-0, MMT cell, tumor cell, and a cell line derived from an aforementioned cell.

Therapeutic Uses

The invention also relates to treating an endothelin-1 related disease or disorder. The method comprises administering a fusion polypeptide of the invention to an individual in need thereof.

The polypeptide may be formulated with pharmaceutically acceptable carriers or diluents as well as known adjuvants and excipients in accordance with conventional techniques such as those disclosed in Remington: The Science and Practice of Pharmacy, 19th Edition, Gennaro, Ed., Mack Publishing Co., Easton, Pa., 1995, and using trial and error experimentation.

The pharmaceutically acceptable carriers or diluents as well as any other known adjuvants and excipients should be suitable for the chosen polypeptide of the present invention and the chosen mode of administration. The actual dosage levels of the active ingredients in the pharmaceutical compositions may be varied so as to obtain an amount of the active ingredient which is effective to achieve the appropriate stability of drug substance, desired therapeutic response for a particular patient, composition, and mode of administration. The selected dosage level will depend upon a variety of pharmacokinetic factors.

The pharmaceutical composition may be administered by any suitable route and mode. Suitable routes of administering a fusion protein in vivo are well known in the art and may be selected by those of ordinary skill in the art (Daugherty, A L, and Msrny, R J, 2006, *Adv Drug Delivery Rev*, 58(5-6): 686-706).

As discussed above, endothelin-1 plays a role in neurodegenerative disorders, diabetes, cardiovascular disorders as well as pregnancy disorders such as pre-eclampsia.

In pre-eclampsia, endothelin-1 is known to mediate hypertension. Antagonism of endothelin-1 has been shown to be beneficial in animal models of gestational hypertension (see e.g. Jain (2012) *Reprod Biomed Online*, 25, 443-449 and George and Granger (2011) *Am J Hpyertens*, 24, 964-969, Saleh et al (2015) *Therpeutic Advances in Cardiovascular Disease*, 10, 282-293).

Endothelin-1 is a potent vasoconstrictor and has been implicated in vascular dysfunction and cardiovascular disease. The ET receptors have been implicated not only in hypertension but also in the development of atherosclerosis, cardiomyopathy and insulin resistance. ET receptor antagonists are approved for the treatment of pulmonary arterial hypertension (see e.g. Bohm et al (2007) *Cardiovascular Research*, 76, 8-18)

Examples

Figure 15A:
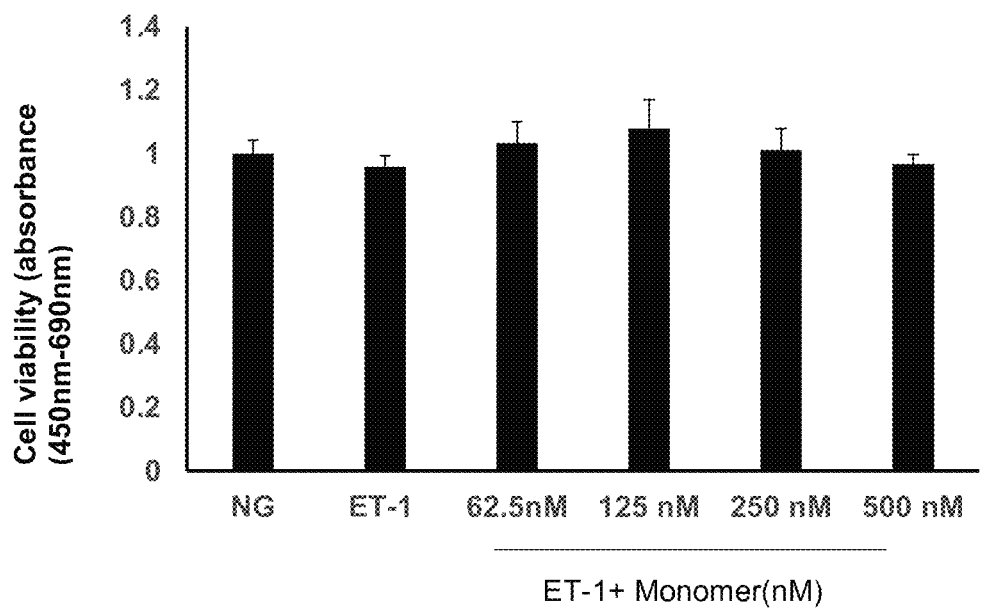
FIG. 15A-B shows cell viability data (mean±SEM using WST assay, expressed as absorbance) normalised to NG (normal glucose; 5 mM glucose). No significant changes were observed in the viability of the cells following incubation with 25 mM glucose (HG) (FIG. 15B) or 10 nM endothelin-1 (ET-1) (FIG. 15A) along with simultaneous incubation with various concentrations of monomeric ET-1 sponge (SEQ ID NO: 1). *$p<0.05$ compared to NG, experiment performed in triplicate from three separate experiments, data expressed as mean±SEM, normalized to NG.
Figure 15B:
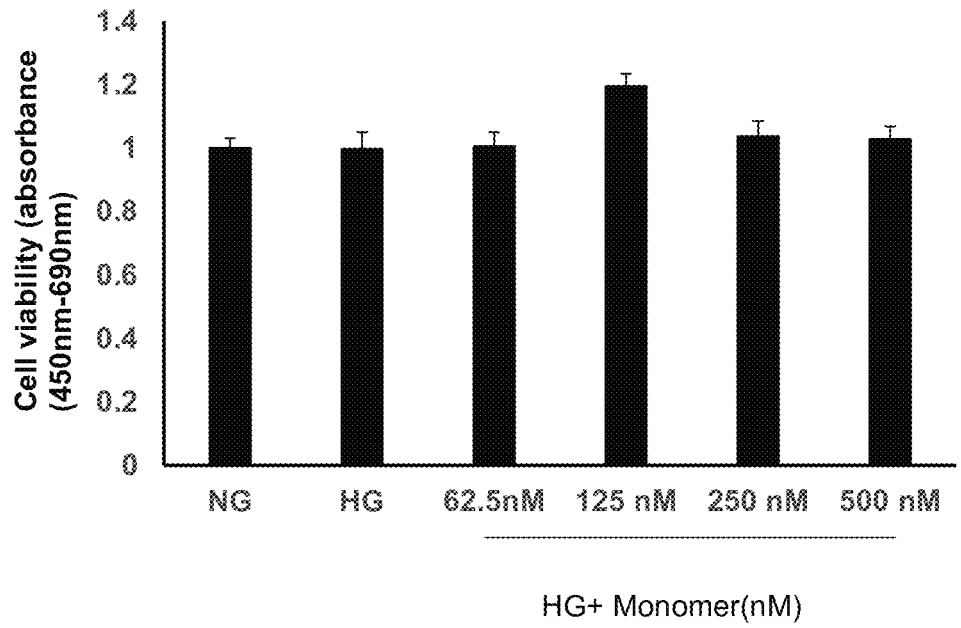
Figure 16A:
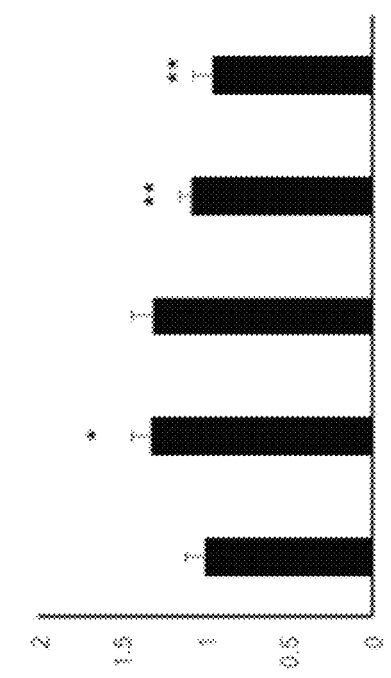
FIG. 16A-D shows real time PCR analysis of fibronectin (FIGS. 16A and 16C) and collagen 4α1 (FIGS. 16B and 16D) transcripts in HRMECs exposed to 25 nM glucose (HG) (FIGS. 16C and 16D) or 10 nM endothelin-1 (ET-1) (FIGS. 16A and 16B). Both transcripts were significantly upregulated in HRMECs after 48 hours incubation with HG and 24 hours incubation with ET-1 compared with HRMECs treated with normal glucose (5 nM; NG) and were prevented following incubation with ET-1 sponge (monomeric). *$p<0.05$ compared to NG. $p<0.05$ compared to HG or ET-1, experiments performed in triplicate from three separate experiments, data expressed as mean±SEM, normalized to NG.
Figure 16B:
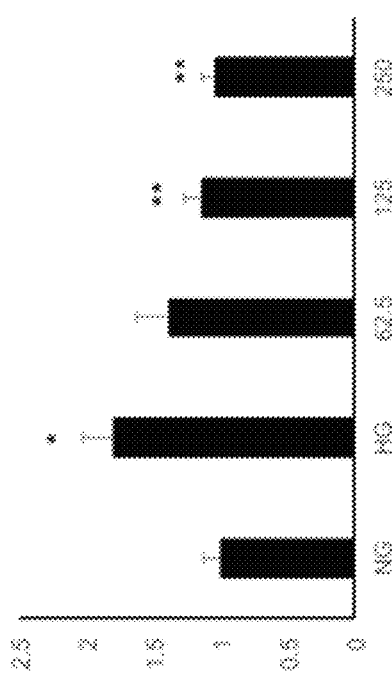
Figure 16C:
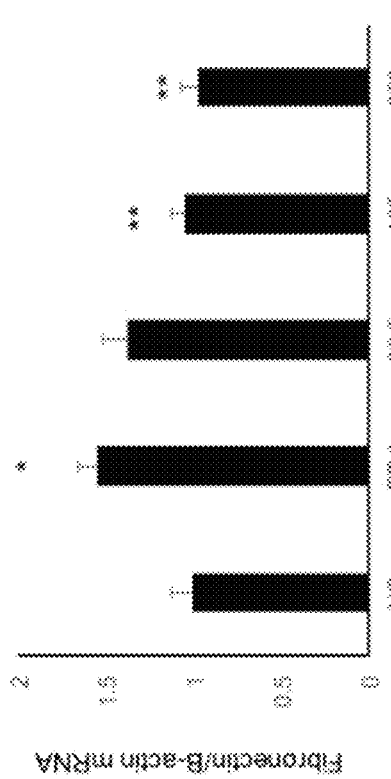
Figure 16D:
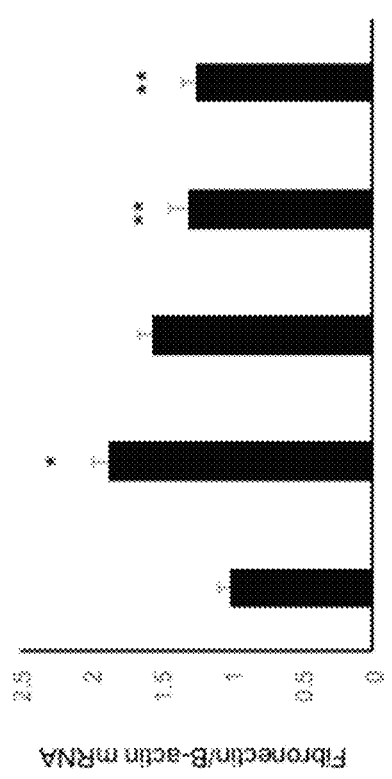

Viability of human retinal microvascular endothelial cells (HRMECs) was investigated after treatment with ET-1 (10 nM) and high glucose (HG; 25 mmol/L). Results are presented in FIG. 15A-B. No difference in viability was observed in cells treated with high glucose or ET-1 for a period of 48 hours. The monomeric ET-1 sponge construct (SEQ ID NO: 1) also showed no cytotoxic effects at various concentrations of up to 500 nM for 24 hours incubation with 25 mmol/L D-glucose or 10 nM ET-1.

Endothelial cells (ECs) line the blood vessels and are critical for function and integrity of the vascular unit. HRMECs were used as an in vitro model to study the effects of the ET-1 sponge construct on expression of protein after ET-1 or high glucose treatment. A dose response assay was performed using 61.25 nM, 125 nM and 250 nM treatments with monomeric ET-1 sponge. Results are presented in FIG. 16A-D.

Based on previous experiments, fibronectin and collagen reach peak at 24 and 48 hours following ET-1 and glucose treatment, respectively. These were therefore used as time points for subsequent analyses. Treatment with either 10 nM ET-1 or high glucose treatment (25 mmol/L) produced a significant increase in the expression of both fibronectin and collagen 4α1 (FIG. 16A-D). Treatment with the monomeric ET-1 sponge construct gave a significant reduction in expression of both ECM proteins back to basal control levels with the 125 nM and 250 nM dose of the ET-1 sponge.

Figure 17A:
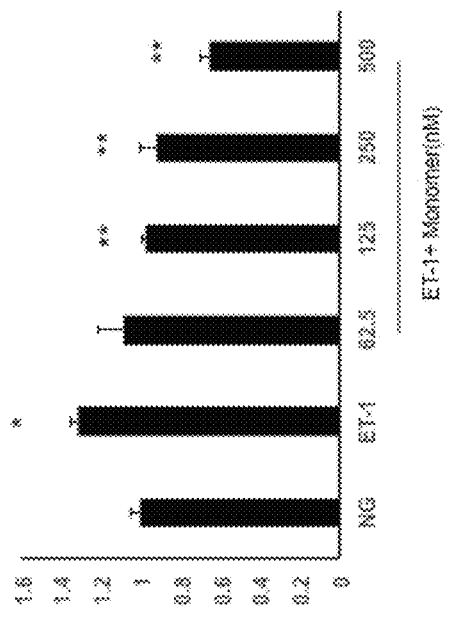
FIG. 17A-D shows protein expression analyses (ELISA) of fibronectin (FIGS. 17A and 17C) and collagen 4α1 (FIGS. 17B and 17D) in HRMECs exposed to 25 nM glucose (HG) (FIGS. 17C and 17D) or 10 nM endothelin-1 (ET-1) (FIGS. 17A and 17B). Both proteins were significantly increased in HRMECs after 48 hours incubation with HG and 24 hours incubation with ET-1 compared with HRMECs treated with normal glucose (5 mM; NG) and were prevented following incubation with ET-1 sponge (monomeric). *$p<0.05$ compared to NG. **$p<0.05$ compared to HG or ET-1, experiments performed in triplicate from three separate experiments, data expressed as mean±SEM, normalized to NG.
Figure 17B:
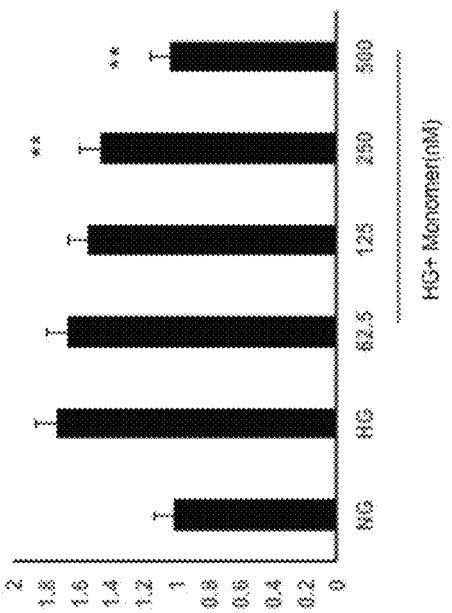
Figure 17C:
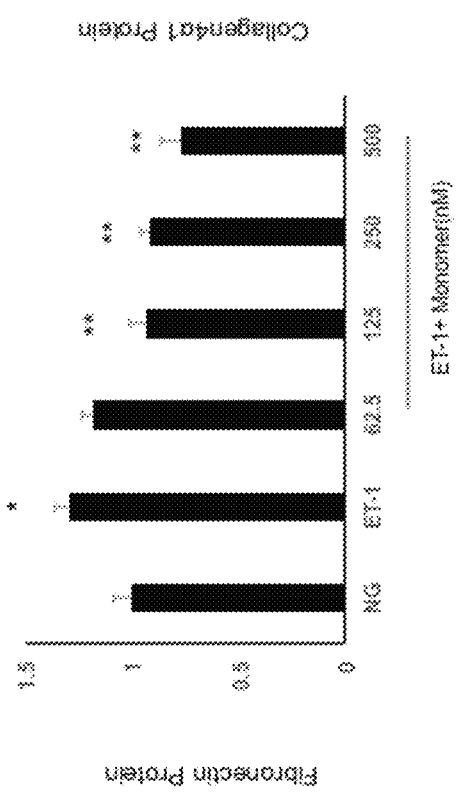
Figure 17D:
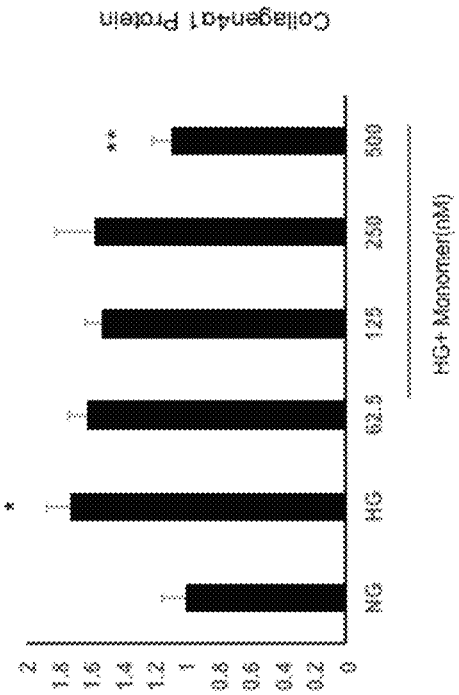

ELISA analysis then revealed that (analogous to mRNA measurements) treating HRMECs with either 10 nM ET-1 or a high glucose treatment (25 mmol/L) both gave a significant increase in protein expression of fibronectin and collagen 4α1. Treatment with various doses of the monomeric ET-1 sponge constructs prevented this increase in expression of both ECM proteins. A significant effect was observed on both ECM proteins with a 125 nM upwards treatment of the ET-1 sponge after treatment with 10 nM ET-1 (FIGS. 17A and B) and with the 500 nM dose of the monomeric ET-1 sponge after high glucose treatment (FIGS. 17C and D).

ASPECTS OF THE INVENTION (24)

1. A fusion polypeptide which is capable of forming a monomer or multimer capable of binding endothelin-1 to form a non-functional complex, wherein the fusion polypeptide comprises the amino acid sequence of SEQ ID NO: 1.

2. A recombinant nucleic acid molecule encoding the fusion polypeptide of aspect 1.

3. A fusion polypeptide which is capable of forming a monomer or multimer capable of binding endothelin-1 to form a non-functional complex, wherein the fusion polypeptide comprises the amino acid sequence of SEQ ID NO: 2.

4. A recombinant nucleic acid molecule encoding the fusion polypeptide of aspect 3.

5. A fusion polypeptide which is capable of forming a monomer or multimer capable of binding endothelin-1 to form a non-functional complex, wherein the fusion polypeptide comprises the amino acid sequence of SEQ ID NO: 3.

6. A recombinant nucleic acid molecule encoding the fusion polypeptide of aspect 5.

7. A fusion polypeptide which is capable of forming a monomer or multimer capable of binding endothelin-1 to form a non-functional complex, wherein the fusion polypeptide comprises the amino acid sequence of SEQ ID NO: 4.

8. A recombinant nucleic acid molecule encoding the fusion polypeptide of aspect 7.

9. A fusion polypeptide which is capable of forming a monomer or multimer capable of binding endothelin-1 to form a non-functional complex, wherein the fusion polypeptide comprises the amino acid sequence of SEQ ID NO: 5.

10. A recombinant nucleic acid molecule encoding the fusion polypeptide of aspect 9.

11. A fusion polypeptide which is capable of forming a monomer or multimer capable of binding endothelin-1 to form a non-functional complex, wherein the fusion polypeptide comprises the amino acid sequence of SEQ ID NO: 6.

12. A recombinant nucleic acid molecule encoding the fusion polypeptide of aspect 1.

13. A fusion polypeptide capable of binding endothelin-1 to form a non-functional complex, wherein the fusion polypeptide comprises one or more of the ETA receptor ligand-binding domains of aspect 1.

14. A fusion polypeptide which is capable of forming a monomer or multimer capable of binding endothelin-1 to form a non-functional complex, wherein the fusion polypeptide comprises the amino acid sequence of SEQ ID NO: 7.

15. A recombinant nucleic acid molecule encoding the fusion polypeptide of aspect 14.

16. A fusion polypeptide which is capable of forming a monomer or multimer capable of binding endothelin-1 to form a non-functional complex, wherein the fusion polypeptide comprises the amino acid sequence of SEQ ID NO: 8.

17. A recombinant nucleic acid molecule encoding the fusion polypeptide of aspect 16.

18. A fusion polypeptide which is capable of forming a monomer or multimer capable of binding endothelin-1 to form a non-functional complex, wherein the fusion polypeptide comprises the amino acid sequence of SEQ ID NO: 9.

19. A recombinant nucleic acid molecule encoding the fusion polypeptide of aspect 18.

20. A fusion polypeptide capable of binding endothelin-1 to form a non-functional complex, wherein the polypeptide molecule comprises one or more of the ETB receptor ligand-binding domains of aspect 16.

21. A composition capable of binding endothelin-1 to form a non-functional complex comprising a monomer or multimer of the fusion polypeptide of any of aspects 1, 3, 5, 7, 9, 11, 14, 16 or 18.

22. The composition of aspect 21, wherein the multimer is a dimer.

23. A vector comprising the nucleic acid molecule of any of aspects 2, 4, 6, 8, 10, 12, 15, 17 or 19.

24. An expression vector comprising the nucleic acid molecule of any of aspects 2, 4, 6, 8, 10, 12, 15, 17 or 19 operatively linked to an expression control sequence.

REFERENCES

The following references were cited in the present specification. The entire contents of each of the following publications are hereby incorporated herein by reference, particularly with respect to the aspects thereof for which they were cited hereinabove.

REFERENCES

Adachi, M., K. Hashido, et al. (1993). "Functional domains of human endothelin receptor." J Cardiovasc Pharmacol 22 Supp 8: S121-124.

Arai, et al. (2001) "Design of the linkers which effectively separate domains of a bifunctional fusion protein" PEDS, 14(8): 529-32

Böhm et al (2007) "The importance of endothelin-1 for vascular dysfunction in cardiovascular disease" Cardiovascular Research, 76, 8-18

Chen, X. et al., (2013) "Fusion protein linkers: property, design and functionality" Advanced Drug Delivery Reviews 65: 1357-1369.

Daugherty, A L, and Msrny, R J (2006) "Formulation and delivery issues for monoclonal antibody therapeutics" Adv Drug Delivery Rev, 58(5-6): 686-706

George and Granger (2011) "Endothelin: key mediator of hypertension in preeclampsia" Am J Hpyertens, 24, 964-969

Haufschild, T., S. G. Shaw, et al. (2001). "Increased endothelin-1 plasma levels in patients with multiple sclerosis." J Neuroophthalmol 21(1): 37-38.

Huston, et al, 1988, PNAS, "Protein engineering of antibody binding sites: recovery of specific activity in an anti-digoxin single-chain Fv analogue produced in Escherichia coli" 85:16:5879-83

Jain, A. (2013). "Endothelin-1-induced endoplasmic reticulum stress in disease." J Pharmacol Exp Ther 346(2): 163-172.

Jain, A., M. Olovsson, et al. (2012). "Endothelin-1 induces endoplasmic reticulum stress by activating the PLC-IP(3) pathway: implications for placental pathophysiology in preeclampsia." Am J Pathol 180(6): 2309-2320.

Jain, A. et al. (2017) Creating a Soluble Binder to Endothelin-1 Based on the Natural Ligand Binding Domains of the Endothelin-1 (G-Protein-Coupled) Receptor. International Journal of Peptide Research and Therapeutics.

Karet, F. E. and A. P. Davenport (1994). "Endothelin and the human kidney: a potential target for new drugs." Nephrol Dial Transplant 9(5): 465-468.

Klammt, C., A. Srivastava, et al. (2007). "Functional analysis of cell-free-produced human endothelin B receptor reveals transmembrane segment 1 as an essential area for ET-1 binding and homodimer formation." FEBS J 274 (13): 3257-3269.

Kost, T; and Condreay, J P, 1999, "Recombinant baculoviruses as expression vectors for insect and mammalian cells", Current Opinion in Biotechnology, 10 (5): 428-33

Nelson, J., A. Bagnato, et al. (2003). "The endothelin axis: emerging role in cancer." Nat Rev Cancer 3(2): 110-116.

Orry, A. J. and B. A. Wallace (2000). "Modeling and docking the endothelin G-protein-coupled receptor." Biophys J 79(6): 3083-3094.

Pache, M., H. J. Kaiser, et al. (2003). "Extraocular blood flow and endothelin-1 plasma levels in patients with multiple sclerosis." Eur Neurol 49(3): 164-168.

Robinson & Bates, 1998, PNAS 95(11):5929-34

Saleh et al (2015) "The emerging role of endothelin-1 in the pathogenesis of pre-eclampsia" Therapeutic Advances in Cardiovascular Disease, 10, 282-293

Schneider, J. G., N. Tilly, et al. (2002). "Elevated plasma endothelin-1 levels in diabetes mellitus." Am J Hypertens 15(11): 967-972.

Seligman, B. G., A. Biolo, et al. (2000). "Increased plasma levels of endothelin 1 and von Willebrand factor in patients with type 2 diabetes and dyslipidemia." Diabetes Care 23(9): 1395-1400.

Sethi, A. S., D. M. Lees, et al. (2006). "Homocysteine-induced endothelin-1 release is dependent on hyperglycaemia and reactive oxygen species production in bovine aortic endothelial cells." J Vasc Res 43(2): 175-183.

Van Heeke & Schuster, 1989, "The N-terminal cysteine of human asparagine synthetase is essential for glutamine-dependent activity" J Biol Chem 264, 5503-5509

Wada, K., K. Hashido, et al. (1995). "Ligand binding domain of the human endothelin-B subtype receptor." Protein Expr Purif 6(3): 228-236.

Wang et al (2016) "Discovery of Dual ETA/ETB Receptor Antagonists from Traditional Chinese Herbs through in Silico and in Vitro Screening" Int J Mol Sci, 17(3):389

Zeiher, A. M., H. Goebel, et al. (1995). "Tissue endothelin-1 immunoreactivity in the active coronary atherosclerotic plaque. A clue to the mechanism of increased vasoreactivity of the culprit lesion in unstable angina." Circulation 91(4): 941-947.

The invention claimed is:

1. A fusion polypeptide comprising the amino acid sequence of the endothelin A receptor ligand binding domains of SEQ ID NO: 1 or the amino acid sequence of the endothelin A receptor ligand binding domains of SEQ ID NO: 2.

2. The fusion polypeptide of claim 1, fused to the Fc portion of human IgG1.

3. The fusion polypeptide of claim 1, in the form of a monomer.

4. The fusion polypeptide of claim 1 in the form of a multimer.

5. The multimer of claim 4, which is a dimer.

6. A composition comprising a fusion polypeptide of claim 1.

7. A recombinant nucleic acid molecule encoding a fusion polypeptide of claim 1.

8. A vector comprising the nucleic acid molecule of claim 7.

9. An expression vector comprising the nucleic acid molecule of claim 7, operatively linked to an expression control sequence.

* * * * *

SEQUENCE LISTING

<160> NUMBER OF SEQ ID NOS: 17

<210> SEQ ID NO 1
<211> LENGTH: 437

<212> TYPE: PRT
<213> ORGANISM: Artificial Sequence
<220> FEATURE:
<223> OTHER INFORMATION: Synthetic

<400> SEQUENCE: 1

Asp Asn Pro Glu Arg Tyr Ser Thr Asn Leu Ser Asn His Val Asp Asp
1               5                   10                  15

Phe Thr Thr Phe Arg Gly Thr Glu Leu Ser Phe Leu Val Thr Thr His
            20                  25                  30

Gln Pro Thr Asn Leu Val Leu Pro Ser Asn Gly Ser Met His Asn Tyr
        35                  40                  45

Cys Pro Gln Gln Thr Lys Ile Thr Ser Ala Phe Lys Lys Leu Leu Ala
50                  55                  60

Gly Arg Trp Pro Phe Asp His Asn Asp Phe Gly Val Phe Leu Cys Pro
65                  70                  75                  80

Phe Glu Tyr Arg Gly Glu Gln His Lys Thr Cys Met Leu Asn Ala Thr
            85                  90                  95

Ser Lys Phe Met Glu Phe Tyr Gln Asp Val Lys Asp Thr Cys Glu Met
            100                 105                 110

Leu Asn Arg Arg Asn Gly Ser Leu Arg Ile Ala Leu Ser Glu His Leu
        115                 120                 125

Lys Gln Arg Arg Glu Val Ala Lys Thr Val Phe Cys Val Tyr Asn Glu
130                 135                 140

Met Asp Lys Asn Arg Cys Glu Leu Leu Ser Phe Leu Ser Lys Lys Phe
145                 150                 155                 160

Lys Asn Cys Phe Gln Ser Cys Leu Cys Cys Cys Tyr Gln Ser Lys
            165                 170                 175

Ser Leu Met Thr Ser Val Pro Met Asn Gly Thr Ser Ile Gln Trp Lys
            180                 185                 190

Asn His Asp Gln Asn Asn His Asn Thr Asp Arg Ser Ser His Lys Asp
        195                 200                 205

Ser Met Asn Lys Thr His Thr Cys Pro Pro Cys Pro Ala Pro Glu Leu
210                 215                 220

Leu Gly Gly Pro Ser Val Phe Leu Phe Pro Pro Lys Pro Lys Asp Thr
225                 230                 235                 240

Leu Met Ile Ser Arg Thr Pro Glu Val Thr Cys Val Val Val Asp Val
            245                 250                 255

Ser His Glu Asp Pro Glu Val Lys Phe Asn Trp Tyr Val Asp Gly Val
        260                 265                 270

Glu Val His Asn Ala Lys Thr Lys Pro Arg Glu Glu Gln Tyr Asn Ser
        275                 280                 285

Thr Tyr Arg Val Val Ser Val Leu Thr Val Leu His Gln Asp Trp Leu
    290                 295                 300

Asn Gly Lys Glu Tyr Lys Cys Lys Val Ser Asn Lys Ala Leu Pro Ala
305                 310                 315                 320

Pro Ile Glu Lys Thr Ile Ser Lys Ala Lys Gly Gln Pro Arg Glu Pro
            325                 330                 335

Gln Val Tyr Thr Leu Pro Pro Ser Arg Glu Glu Met Thr Lys Asn Gln
        340                 345                 350

Val Ser Leu Thr Cys Leu Val Lys Gly Phe Tyr Pro Ser Asp Ile Ala
        355                 360                 365

Val Glu Trp Glu Ser Asn Gly Gln Pro Glu Asn Asn Tyr Lys Thr Thr
    370                 375                 380

```
Pro Pro Val Leu Asp Ser Asp Gly Ser Phe Phe Leu Tyr Ser Lys Leu
385                 390                 395                 400

Thr Val Asp Lys Ser Arg Trp Gln Gln Gly Asn Val Phe Ser Cys Ser
            405                 410                 415

Val Met His Glu Ala Leu His Asn His Tyr Thr Gln Lys Ser Leu Ser
        420                 425                 430

Leu Ser Pro Gly Lys
        435

<210> SEQ ID NO 2
<211> LENGTH: 374
<212> TYPE: PRT
<213> ORGANISM: Artificial Sequence
<220> FEATURE:
<223> OTHER INFORMATION: Synthetic

<400> SEQUENCE: 2

Asp Asn Pro Glu Arg Tyr Ser Thr Asn Leu Ser Asn His Val Asp Asp
1               5                   10                  15

Phe Thr Thr Phe Arg Gly Thr Glu Leu Ser Phe Leu Val Thr Thr His
                20                  25                  30

Gln Pro Thr Asn Leu Val Leu Pro Ser Asn Gly Ser Met His Asn Tyr
            35                  40                  45

Cys Pro Gln Gln Thr Lys Ile Thr Ser Ala Phe Lys Lys Leu Leu Ala
50                  55                  60

Gly Arg Trp Pro Phe Asp His Asn Asp Phe Gly Val Phe Leu Cys Pro
65                  70                  75                  80

Phe Glu Tyr Arg Gly Glu Gln His Lys Thr Cys Met Leu Asn Ala Thr
                85                  90                  95

Ser Lys Phe Met Glu Phe Tyr Gln Asp Val Lys Asp Ser Glu His Leu
            100                 105                 110

Lys Gln Arg Arg Glu Val Ala Lys Thr Val Phe Cys Val Tyr Asn Glu
        115                 120                 125

Met Asp Lys Asn Arg Cys Glu Leu Leu Ser Phe Leu Ser Lys Lys Phe
130                 135                 140

Lys Asn Cys Phe Lys Thr His Thr Cys Pro Pro Cys Pro Ala Pro Glu
145                 150                 155                 160

Leu Leu Gly Gly Pro Ser Val Phe Leu Phe Pro Pro Lys Pro Lys Asp
                165                 170                 175

Thr Leu Met Ile Ser Arg Thr Pro Glu Val Thr Cys Val Val Val Asp
            180                 185                 190

Val Ser His Glu Asp Pro Glu Val Lys Phe Asn Trp Tyr Val Asp Gly
        195                 200                 205

Val Glu Val His Asn Ala Lys Thr Lys Pro Arg Glu Glu Gln Tyr Asn
210                 215                 220

Ser Thr Tyr Arg Val Val Ser Val Leu Thr Val Leu His Gln Asp Trp
225                 230                 235                 240

Leu Asn Gly Lys Glu Tyr Lys Cys Lys Val Ser Asn Lys Ala Leu Pro
                245                 250                 255

Ala Pro Ile Glu Lys Thr Ile Ser Lys Ala Lys Gly Gln Pro Arg Glu
            260                 265                 270

Pro Gln Val Tyr Thr Leu Pro Pro Ser Arg Glu Glu Met Thr Lys Asn
        275                 280                 285

Gln Val Ser Leu Thr Cys Leu Val Lys Gly Phe Tyr Pro Ser Asp Ile
290                 295                 300
```

```
Ala Val Glu Trp Glu Ser Asn Gly Gln Pro Glu Asn Asn Tyr Lys Thr
305                 310                 315                 320

Thr Pro Pro Val Leu Asp Ser Asp Gly Ser Phe Phe Leu Tyr Ser Lys
            325                 330                 335

Leu Thr Val Asp Lys Ser Arg Trp Gln Gln Gly Asn Val Phe Ser Cys
            340                 345                 350

Ser Val Met His Glu Ala Leu His Asn His Tyr Thr Gln Lys Ser Leu
        355                 360                 365

Ser Leu Ser Pro Gly Lys
        370
```

<210> SEQ ID NO 3
<211> LENGTH: 421
<212> TYPE: PRT
<213> ORGANISM: Artificial Sequence
<220> FEATURE:
<223> OTHER INFORMATION: Synthetic

<400> SEQUENCE: 3

```
Asp Asn Pro Glu Arg Tyr Ser Thr Asn Leu Ser Asn His Val Asp Asp
1               5                   10                  15

Phe Thr Thr Phe Arg Gly Thr Glu Leu Ser Phe Leu Val Thr Thr His
            20                  25                  30

Gln Pro Thr Asn Leu Val Leu Pro Ser Asn Gly Ser Met His Asn Tyr
        35                  40                  45

Cys Pro Gln Gln Thr Lys Ile Thr Ser Ala Phe Lys Lys Leu Leu Ala
    50                  55                  60

Gly Arg Trp Pro Phe Asp His Asn Asp Phe Gly Val Phe Leu Cys Pro
65                  70                  75                  80

Phe Glu Tyr Arg Gly Glu Gln His Lys Thr Cys Met Leu Asn Ala Thr
                85                  90                  95

Ser Lys Phe Met Glu Phe Tyr Gln Asp Val Lys Asp Thr Cys Glu Met
            100                 105                 110

Leu Asn Arg Arg Asn Gly Ser Leu Arg Ile Ala Leu Ser Glu His Leu
        115                 120                 125

Lys Gln Arg Arg Glu Val Ala Lys Thr Val Phe Cys Ser Lys Lys Phe
    130                 135                 140

Lys Asn Cys Phe Gln Ser Cys Leu Cys Cys Cys Tyr Gln Ser Lys
145                 150                 155                 160

Ser Leu Met Thr Ser Val Pro Met Asn Gly Thr Ser Ile Gln Trp Lys
                165                 170                 175

Asn His Asp Gln Asn Asn His Asn Thr Asp Arg Ser Ser His Lys Asp
            180                 185                 190

Ser Met Asn Lys Thr His Thr Cys Pro Pro Cys Pro Ala Pro Glu Leu
        195                 200                 205

Leu Gly Gly Pro Ser Val Phe Leu Phe Pro Pro Lys Pro Lys Asp Thr
    210                 215                 220

Leu Met Ile Ser Arg Thr Pro Glu Val Thr Cys Val Val Val Asp Val
225                 230                 235                 240

Ser His Glu Asp Pro Glu Val Lys Phe Asn Trp Tyr Val Asp Gly Val
                245                 250                 255

Glu Val His Asn Ala Lys Thr Lys Pro Arg Glu Glu Gln Tyr Asn Ser
            260                 265                 270

Thr Tyr Arg Val Val Ser Val Leu Thr Val Leu His Gln Asp Trp Leu
        275                 280                 285
```

```
Asn Gly Lys Glu Tyr Lys Cys Lys Val Ser Asn Lys Ala Leu Pro Ala
    290                 295                 300

Pro Ile Glu Lys Thr Ile Ser Lys Ala Lys Gly Gln Pro Arg Glu Pro
305                 310                 315                 320

Gln Val Tyr Thr Leu Pro Pro Ser Arg Glu Glu Met Thr Lys Asn Gln
                325                 330                 335

Val Ser Leu Thr Cys Leu Val Lys Gly Phe Tyr Pro Ser Asp Ile Ala
                340                 345                 350

Val Glu Trp Glu Ser Asn Gly Gln Pro Glu Asn Asn Tyr Lys Thr Thr
                355                 360                 365

Pro Pro Val Leu Asp Ser Asp Gly Ser Phe Phe Leu Tyr Ser Lys Leu
370                 375                 380

Thr Val Asp Lys Ser Arg Trp Gln Gln Gly Asn Val Phe Ser Cys Ser
385                 390                 395                 400

Val Met His Glu Ala Leu His Asn His Tyr Thr Gln Lys Ser Leu Ser
                405                 410                 415

Leu Ser Pro Gly Lys
            420

<210> SEQ ID NO 4
<211> LENGTH: 358
<212> TYPE: PRT
<213> ORGANISM: Artificial Sequence
<220> FEATURE:
<223> OTHER INFORMATION: Synthetic

<400> SEQUENCE: 4

Asp Asn Pro Glu Arg Tyr Ser Thr Asn Leu Ser Asn His Val Asp Asp
1               5                   10                  15

Phe Thr Thr Phe Arg Gly Thr Glu Leu Ser Phe Leu Val Thr Thr His
                20                  25                  30

Gln Pro Thr Asn Leu Val Leu Pro Ser Asn Gly Ser Met His Asn Tyr
                35                  40                  45

Cys Pro Gln Gln Thr Lys Ile Thr Ser Ala Phe Lys Lys Leu Leu Ala
    50                  55                  60

Gly Arg Trp Pro Phe Asp His Asn Asp Phe Gly Val Phe Leu Cys Pro
65                  70                  75                  80

Phe Glu Tyr Arg Gly Glu Gln His Lys Thr Cys Met Leu Asn Ala Thr
                85                  90                  95

Ser Lys Phe Met Glu Phe Tyr Gln Asp Val Lys Asp Ser Glu His Leu
                100                 105                 110

Lys Gln Arg Arg Glu Val Ala Lys Thr Val Phe Cys Ser Lys Lys Phe
            115                 120                 125

Lys Asn Cys Phe Lys Thr His Thr Cys Pro Pro Cys Pro Ala Pro Glu
    130                 135                 140

Leu Leu Gly Gly Pro Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
                180                 185                 190

Val Glu Val His Asn Ala Lys Thr Lys Pro Arg Glu Glu Gln Tyr Asn
            195                 200                 205

Ser Thr Tyr Arg Val Val Ser Val Leu Thr Val Leu His Gln Asp Trp
    210                 215                 220
```

```
Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Glu Glu Met Thr Lys Asn
            260                 265                 270

Gln Val Ser Leu Thr Cys Leu Val Lys Gly Phe Tyr Pro Ser Asp Ile
        275                 280                 285

Ala Val Glu Trp Glu Ser Asn Gly Gln Pro Glu Asn Asn Tyr Lys Thr
    290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly Lys
        355

<210> SEQ ID NO 5
<211> LENGTH: 408
<212> TYPE: PRT
<213> ORGANISM: Artificial Sequence
<220> FEATURE:
<223> OTHER INFORMATION: Synthetic

<400> SEQUENCE: 5

Asp Asn Pro Glu Arg Tyr Ser Thr Asn Leu Ser Asn His Val Asp Asp
1               5                   10                  15

Phe Thr Thr Phe Arg Gly Thr Glu Leu Ser Phe Leu Val Thr Thr His
                20                  25                  30

Gln Pro Thr Asn Leu Val Leu Pro Ser Asn Gly Ser Met His Asn Tyr
            35                  40                  45

Cys Pro Gln Gln Thr Lys Ile Thr Ser Ala Phe Lys Lys Leu Leu Ala
    50                  55                  60

Gly Arg Trp Pro Phe Asp His Asn Asp Phe Gly Val Phe Leu Cys Thr
65                  70                  75                  80

Cys Glu Met Leu Asn Arg Arg Asn Gly Ser Leu Arg Ile Ala Leu Ser
                85                  90                  95

Glu His Leu Lys Gln Arg Arg Glu Val Ala Lys Thr Val Phe Cys Val
            100                 105                 110

Tyr Asn Glu Met Asp Lys Asn Arg Cys Glu Leu Leu Ser Phe Leu Ser
        115                 120                 125

Lys Lys Phe Lys Asn Cys Phe Gln Ser Cys Leu Cys Cys Cys Cys Tyr
130                 135                 140

Gln Ser Lys Ser Leu Met Thr Ser Val Pro Met Asn Gly Thr Ser Ile
145                 150                 155                 160

Gln Trp Lys Asn His Asp Gln Asn Asn His Asn Thr Asp Arg Ser Ser
                165                 170                 175

His Lys Asp Ser Met Asn Lys Thr His Thr Cys Pro Pro Cys Pro Ala
            180                 185                 190

Pro Glu Leu Leu Gly Gly Pro Ser Val Phe Leu Phe Pro Pro Lys Pro
        195                 200                 205

Lys Asp Thr Leu Met Ile Ser Arg Thr Pro Glu Val Thr Cys Val Val
    210                 215                 220
```

Val Asp Val Ser His Glu Asp Pro Glu Val Lys Phe Asn Trp Tyr Val
225                 230                 235                 240

Asp Gly Val Glu Val His Asn Ala Lys Thr Lys Pro Arg Glu Glu Gln
            245                 250                 255

Tyr Asn Ser Thr Tyr Arg Val Val Ser Val Leu Thr Val Leu His Gln
                260                 265                 270

Asp Trp Leu Asn Gly Lys Glu Tyr Lys Cys Lys Val Ser Asn Lys Ala
            275                 280                 285

Leu Pro Ala Pro Ile Glu Lys Thr Ile Ser Lys Ala Lys Gly Gln Pro
        290                 295                 300

Arg Glu Pro Gln Val Tyr Thr Leu Pro Pro Ser Arg Glu Glu Met Thr
305                 310                 315                 320

Lys Asn Gln Val Ser Leu Thr Cys Leu Val Lys Gly Phe Tyr Pro Ser
                325                 330                 335

Asp Ile Ala Val Glu Trp Glu Ser Asn Gly Gln Pro Glu Asn Asn Tyr
            340                 345                 350

Lys Thr Thr Pro Pro Val Leu Asp Ser Asp Gly Ser Phe Phe Leu Tyr
        355                 360                 365

Ser Lys Leu Thr Val Asp Lys Ser Arg Trp Gln Gln Gly Asn Val Phe
370                 375                 380

Ser Cys Ser Val Met His Glu Ala Leu His Asn His Tyr Thr Gln Lys
385                 390                 395                 400

Ser Leu Ser Leu Ser Pro Gly Lys
                405

<210> SEQ ID NO 6
<211> LENGTH: 345
<212> TYPE: PRT
<213> ORGANISM: Artificial Sequence
<220> FEATURE:
<223> OTHER INFORMATION: Synthetic

<400> SEQUENCE: 6

Asp Asn Pro Glu Arg Tyr Ser Thr Asn Leu Ser Asn His Val Asp Asp
1               5                   10                  15

Phe Thr Thr Phe Arg Gly Thr Glu Leu Ser Phe Leu Val Thr Thr His
            20                  25                  30

Gln Pro Thr Asn Leu Val Leu Pro Ser Asn Gly Ser Met His Asn Tyr
        35                  40                  45

Cys Pro Gln Gln Thr Lys Ile Thr Ser Ala Phe Lys Lys Leu Leu Ala
    50                  55                  60

Gly Arg Trp Pro Phe Asp His Asn Asp Phe Gly Val Phe Leu Cys Ser
65                  70                  75                  80

Glu His Leu Lys Gln Arg Arg Glu Val Ala Lys Thr Val Phe Cys Val
                85                  90                  95

Tyr Asn Glu Met Asp Lys Asn Arg Cys Glu Leu Leu Ser Phe Leu Ser
            100                 105                 110

Lys Lys Phe Lys Asn Cys Phe Lys Thr His Thr Cys Pro Pro Cys Pro
        115                 120                 125

Ala Pro Glu Leu Leu Gly Gly Pro Ser Val Phe Leu Phe Pro Pro Lys
    130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

```
Val Asp Gly Val Glu Val His Asn Ala Lys Thr Lys Pro Arg Glu Glu
            180                 185                 190

Gln Tyr Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
    210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Glu Glu Met
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
        275                 280                 285

Tyr Lys Thr Thr Pro Pro Val Leu Asp Ser Asp Gly Ser Phe Phe Leu
    290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
            340                 345

<210> SEQ ID NO 7
<211> LENGTH: 277
<212> TYPE: PRT
<213> ORGANISM: Artificial Sequence
<220> FEATURE:
<223> OTHER INFORMATION: Synthetic

<400> SEQUENCE: 7

Pro Ile Glu Ile Lys Glu Thr Phe Lys Tyr Ile Asn Thr Val Val Ser
1               5                   10                  15

Cys Leu Val Phe Val Leu Gly Ile Ile Gly Asn Ser Thr Leu Leu Arg
            20                  25                  30

Ile Ile Tyr Lys Asn Lys Cys Ser Lys Arg Phe Lys Asn Cys Phe Lys
        35                  40                  45

Ser Cys Leu Lys Thr His Thr Cys Pro Pro Cys Pro Ala Pro Glu Leu
    50                  55                  60

Leu Gly Gly Pro Ser Val Phe Leu Phe Pro Pro Lys Pro Lys Asp Thr
65                  70                  75                  80

Leu Met Ile Ser Arg Thr Pro Glu Val Thr Cys Val Val Val Asp Val
                85                  90                  95

Ser His Glu Asp Pro Glu Val Lys Phe Asn Trp Tyr Val Asp Gly Val
            100                 105                 110

Glu Val His Asn Ala Lys Thr Lys Pro Arg Glu Glu Gln Tyr Asn Ser
        115                 120                 125

Thr Tyr Arg Val Val Ser Val Leu Thr Val Leu His Gln Asp Trp Leu
    130                 135                 140

Asn Gly Lys Glu Tyr Lys Cys Lys Val Ser Asn Lys Ala Leu Pro Ala
145                 150                 155                 160

Pro Ile Glu Lys Thr Ile Ser Lys Ala Lys Gly Gln Pro Arg Glu Pro
                165                 170                 175

Gln Val Tyr Thr Leu Pro Pro Ser Arg Glu Glu Met Thr Lys Asn Gln
            180                 185                 190
```

Val Ser Leu Thr Cys Leu Val Lys Gly Phe Tyr Pro Ser Asp Ile Ala
            195                 200                 205

Val Glu Trp Glu Ser Asn Gly Gln Pro Glu Asn Asn Tyr Lys Thr Thr
    210                 215                 220

Pro Pro Val Leu Asp Ser Asp Gly Ser Phe Phe Leu Tyr Ser Lys Leu
225                 230                 235                 240

Thr Val Asp Lys Ser Arg Trp Gln Gln Gly Asn Val Phe Ser Cys Ser
            245                 250                 255

Val Met His Glu Ala Leu His Asn His Tyr Thr Gln Lys Ser Leu Ser
            260                 265                 270

Leu Ser Pro Gly Lys
        275

<210> SEQ ID NO 8
<211> LENGTH: 337
<212> TYPE: PRT
<213> ORGANISM: Artificial Sequence
<220> FEATURE:
<223> OTHER INFORMATION: Synthetic

<400> SEQUENCE: 8

Pro Ile Glu Ile Lys Glu Thr Phe Lys Tyr Ile Asn Thr Val Val Ser
1               5                   10                  15

Cys Leu Val Phe Val Leu Gly Ile Ile Gly Asn Ser Thr Leu Leu Arg
            20                  25                  30

Ile Ile Tyr Lys Asn Lys Cys Ile Leu Ile Ala Ser Leu Ala Leu Gly
        35                  40                  45

Asp Leu Leu His Ile Val Ile Asp Ile Pro Ile Asn Val Tyr Lys Leu
    50                  55                  60

Leu Ala Glu Asp Trp Pro Phe Gly Ala Glu Met Cys Lys Leu Val Pro
65                  70                  75                  80

Phe Ile Gln Lys Ala Ser Val Gly Ile Thr Val Leu Ser Leu Cys Ala
            85                  90                  95

Leu Ser Ile Ser Lys Arg Phe Lys Asn Cys Phe Lys Ser Cys Leu Lys
            100                 105                 110

Thr His Thr Cys Pro Pro Cys Pro Ala Pro Glu Leu Leu Gly Gly Pro
        115                 120                 125

Ser Val Phe Leu Phe Pro Pro Lys Pro Lys Asp Thr Leu Met Ile Ser
    130                 135                 140

Arg Thr Pro Glu Val Thr Cys Val Val Val Asp Val Ser His Glu Asp
145                 150                 155                 160

Pro Glu Val Lys Phe Asn Trp Tyr Val Asp Gly Val Glu Val His Asn
            165                 170                 175

Ala Lys Thr Lys Pro Arg Glu Glu Gln Tyr Asn Ser Thr Tyr Arg Val
        180                 185                 190

Val Ser Val Leu Thr Val Leu His Gln Asp Trp Leu Asn Gly Lys Glu
    195                 200                 205

Tyr Lys Cys Lys Val Ser Asn Lys Ala Leu Pro Ala Pro Ile Glu Lys
210                 215                 220

Thr Ile Ser Lys Ala Lys Gly Gln Pro Arg Glu Pro Gln Val Tyr Thr
225                 230                 235                 240

Leu Pro Pro Ser Arg Glu Glu Met Thr Lys Asn Gln Val Ser Leu Thr
            245                 250                 255

Cys Leu Val Lys Gly Phe Tyr Pro Ser Asp Ile Ala Val Glu Trp Glu
            260                 265                 270

```
Ser Asn Gly Gln Pro Glu Asn Tyr Lys Thr Thr Pro Val Leu
            275                 280                 285

Asp Ser Asp Gly Ser Phe Phe Leu Tyr Ser Lys Leu Thr Val Asp Lys
290                 295                 300

Ser Arg Trp Gln Gln Gly Asn Val Phe Ser Cys Ser Val Met His Glu
305                 310                 315                 320

Ala Leu His Asn His Tyr Thr Gln Lys Ser Leu Ser Leu Ser Pro Gly
            325                 330                 335

Lys

<210> SEQ ID NO 9
<211> LENGTH: 265
<212> TYPE: PRT
<213> ORGANISM: Artificial Sequence
<220> FEATURE:
<223> OTHER INFORMATION: Synthetic

<400> SEQUENCE: 9

Pro Ile Glu Ile Lys Glu Thr Phe Lys Tyr Ile Asn Thr Val Val Ser
1               5                   10                  15

Cys Leu Val Phe Val Leu Gly Ile Ile Gly Asn Ser Thr Leu Leu Arg
            20                  25                  30

Ile Ile Tyr Lys Asn Lys Cys Lys Thr His Thr Cys Pro Pro Cys Pro
        35                  40                  45

Ala Pro Glu Leu Leu Gly Gly Pro Ser Val Phe Leu Phe Pro Pro Lys
    50                  55                  60

Pro Lys Asp Thr Leu Met Ile Ser Arg Thr Pro Glu Val Thr Cys Val
65                  70                  75                  80

Val Val Asp Val Ser His Glu Asp Pro Glu Val Lys Phe Asn Trp Tyr
                85                  90                  95

Val Asp Gly Val Glu Val His Asn Ala Lys Thr Lys Pro Arg Glu Glu
            100                 105                 110

Gln Tyr Asn Ser Thr Tyr Arg Val Val Ser Val Leu Thr Val Leu His
        115                 120                 125

Gln Asp Trp Leu Asn Gly Lys Glu Tyr Lys Cys Lys Val Ser Asn Lys
130                 135                 140

Ala Leu Pro Ala Pro Ile Glu Lys Thr Ile Ser Lys Ala Lys Gly Gln
145                 150                 155                 160

Pro Arg Glu Pro Gln Val Tyr Thr Leu Pro Pro Ser Arg Glu Glu Met
                165                 170                 175

Thr Lys Asn Gln Val Ser Leu Thr Cys Leu Val Lys Gly Phe Tyr Pro
            180                 185                 190

Ser Asp Ile Ala Val Glu Trp Glu Ser Asn Gly Gln Pro Glu Asn Asn
        195                 200                 205

Tyr Lys Thr Thr Pro Pro Val Leu Asp Ser Asp Gly Ser Phe Phe Leu
210                 215                 220

Tyr Ser Lys Leu Thr Val Asp Lys Ser Arg Trp Gln Gln Gly Asn Val
225                 230                 235                 240

Phe Ser Cys Ser Val Met His Glu Ala Leu His Asn His Tyr Thr Gln
                245                 250                 255

Lys Ser Leu Ser Leu Ser Pro Gly Lys
            260                 265

<210> SEQ ID NO 10
<211> LENGTH: 9
<212> TYPE: PRT
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(9)
<223> OTHER INFORMATION: anyone or all of amino acid residues 5-9 can
      either be present or absent

<400> SEQUENCE: 10

Gly Gly Gly Gly Gly Gly Gly Gly Gly
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Residue 5 can be present or absent

<400> SEQUENCE: 11

Ser Gly Gly Gly Gly
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Any one or all of residues 1-2 can be present
      or absent

<400> SEQUENCE: 12

Gly Gly Gly Gly Gly Ser
1               5

<210> SEQ ID NO 13
<211> LENGTH: 50
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: all residues either present or absent
<220> FEATURE:
<221> NAME/KEY: misc_feature
<222> LOCATION: (11)..(15)
<223> OTHER INFORMATION: all residues either present or absent
<220> FEATURE:
<221> NAME/KEY: misc_feature
<222> LOCATION: (16)..(20)
<223> OTHER INFORMATION: all residues either present or absent
<220> FEATURE:
<221> NAME/KEY: misc_feature
<222> LOCATION: (21)..(25)
<223> OTHER INFORMATION: all residues either present or absent
<220> FEATURE:
<221> NAME/KEY: misc_feature
<222> LOCATION: (26)..(30)
<223> OTHER INFORMATION: all residues either present or absent
<220> FEATURE:
<221> NAME/KEY: misc_feature
<222> LOCATION: (31)..(35)
```

```
<223> OTHER INFORMATION: all residues either present or absent
<220> FEATURE:
<221> NAME/KEY: misc_feature
<222> LOCATION: (36)..(40)
<223> OTHER INFORMATION: all residues either present or absent
<220> FEATURE:
<221> NAME/KEY: misc_feature
<222> LOCATION: (41)..(45)
<223> OTHER INFORMATION: all residues either present or absent
<220> FEATURE:
<221> NAME/KEY: misc_feature
<222> LOCATION: (46)..(50)
<223> OTHER INFORMATION: all residues either present or absent

<400> SEQUENCE: 13

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
                20                  25                  30

Gly Gly Ser Gly Gly Gly Gly Ser Gly Gly Gly Ser Gly Gly
            35                  40                  45

Gly Ser
    50

<210> SEQ ID NO 14
<211> LENGTH: 50
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: all residues either present or absent
<220> FEATURE:
<221> NAME/KEY: misc_feature
<222> LOCATION: (11)..(15)
<223> OTHER INFORMATION: all residues either present or absent
<220> FEATURE:
<221> NAME/KEY: misc_feature
<222> LOCATION: (16)..(20)
<223> OTHER INFORMATION: all residues either present or absent
<220> FEATURE:
<221> NAME/KEY: misc_feature
<222> LOCATION: (21)..(25)
<223> OTHER INFORMATION: all residues either present or absent
<220> FEATURE:
<221> NAME/KEY: misc_feature
<222> LOCATION: (26)..(30)
<223> OTHER INFORMATION: all residues either present or absent
<220> FEATURE:
<221> NAME/KEY: misc_feature
<222> LOCATION: (31)..(35)
<223> OTHER INFORMATION: all residues either present or absent
<220> FEATURE:
<221> NAME/KEY: misc_feature
<222> LOCATION: (36)..(40)
<223> OTHER INFORMATION: all residues either present or absent
<220> FEATURE:
<221> NAME/KEY: misc_feature
<222> LOCATION: (41)..(45)
<223> OTHER INFORMATION: all residues either present or absent
<220> FEATURE:
<221> NAME/KEY: misc_feature
<222> LOCATION: (46)..(50)
<223> OTHER INFORMATION: all residues either present or absent

<400> SEQUENCE: 14

Ser Gly Gly Gly Gly Ser Gly Gly Gly Ser Gly Gly Gly Ser
1               5                   10                  15

Gly Gly Gly Gly Ser Gly Gly Gly Gly Ser Gly Gly Gly Ser Gly
                20                  25                  30
```

-continued

```
Gly Gly Gly Ser Gly Gly Gly Gly Ser Gly Gly Gly Gly Ser Gly Gly
        35                  40                  45

Gly Gly
    50

<210> SEQ ID NO 15
<211> LENGTH: 6
<212> TYPE: PRT
<213> ORGANISM: Artificial Sequence
<220> FEATURE:
<223> OTHER INFORMATION: Synthetic

<400> SEQUENCE: 15

Ser Gly Gly Gly Gly Gly
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic

<400> SEQUENCE: 16

Gly Gly Gly Gly Gly Gly Ser
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic

<400> SEQUENCE: 17

Ser Gly Gly Gly Gly Gly Gly
1               5
```